United States Patent
Curley et al.

(10) Patent No.: US 10,029,972 B2
(45) Date of Patent: Jul. 24, 2018

(54) USE OF HETEROLEPTIC INDIUM HYDROXIDES AS PRECURSORS FOR INP NANOCRYSTALS

(71) Applicant: NANOSYS, Inc., Milpitas, CA (US)

(72) Inventors: John J. Curley, San Francisco, CA (US); Tim Slugocki, San Jose, CA (US); Charlie Hotz, San Rafael, CA (US)

(73) Assignee: Nanosys, Inc., Milpitas, CA (US)

( * ) Notice: Subject to any disclaimer, the term of this patent is extended or adjusted under 35 U.S.C. 154(b) by 90 days.

(21) Appl. No.: 15/348,540

(22) Filed: Nov. 10, 2016

(65) Prior Publication Data

US 2017/0137360 A1 May 18, 2017

Related U.S. Application Data

(60) Provisional application No. 62/255,121, filed on Nov. 13, 2015.

(51) Int. Cl.

| | |
|---|---|
| *C07C 51/02* | (2006.01) |
| *C09K 11/08* | (2006.01) |
| *C01B 25/08* | (2006.01) |
| *C09K 11/70* | (2006.01) |
| *C07C 53/10* | (2006.01) |
| *H01L 21/02* | (2006.01) |
| *C07F 5/00* | (2006.01) |

(52) U.S. Cl.
CPC ............ *C07C 51/02* (2013.01); *C01B 25/087* (2013.01); *C01B 25/088* (2013.01); *C07C 53/10* (2013.01); *C07F 5/003* (2013.01); *C07F 5/006* (2013.01); *C09K 11/0883* (2013.01); *C09K 11/70* (2013.01); *H01L 21/02543* (2013.01)

(58) Field of Classification Search
CPC ..... C01B 25/087; C01B 25/088; C07C 51/02; C07C 53/10; C09K 11/0883; C09K 11/70; H01L 21/02543; C07F 5/003; C07F 5/006
See application file for complete search history.

(56) References Cited

U.S. PATENT DOCUMENTS

| | | | |
|---|---|---|---|
| 5,505,928 | A | 4/1996 | Alivisatos et al. |
| 6,306,736 | B1 | 10/2001 | Alivisatos et al. |
| 6,576,291 | B2 | 6/2003 | Bawendi et al. |
| 6,821,337 | B2 | 11/2004 | Bawendi et al. |
| 7,138,098 | B2 | 11/2006 | Bawendi et al. |
| 2003/0214699 | A1 | 11/2003 | Bann et al. |

FOREIGN PATENT DOCUMENTS

| | | |
|---|---|---|
| DE | 10 2006 059216 A1 | 6/2008 |
| WO | WO 03/054953 A1 | 7/2003 |

OTHER PUBLICATIONS

Allen, P. M., et al., "Mechanistic Insights into the Formation of InP Quantum Dots," *Angew. Chem. Int. Ed.* 49:760-762, Verlag GmbH & Co., Germany (2010).
Beletskaya, I.P., et al., "New Approach to Phosphinoalkynes Based on Pd- and Ni-Catalyzed Cross-Coupling of Terminal Alkynes with Chlorophosphanes," *Organic Letters* 5(23):4309-4311, American Chemical Society, United States (2003).
Farina, V. and Krishnan, B., "Large Rate Accelerations in the Stille Reaction with Tri-2-furylphosphine and Triphenylarsine as Palladium Ligands: Mechanistic and Synthetic Implications," *J. Am. Chem. Soc.* 113:9585-9595, American Chemical Society, United States (1991).
Guzelian, A.A., et al., "Colloidal chemical synthesis and characterization of InAs nanocrystal quantum dots," *Appl. Phys. Lett.* 69:1432-1434, American Institute of Physics, United States (1996).
Guzelian, A.A., et al., "Synthesis of Size-Selected, Surface-Passivated InP Nanocrystals," *J. Phys. Chem.* 100:7212-7219, American Chemical Society, United States (1996).
Kost, D., et al., "The Barrier to Carbon-Phosphorus Bond Rotation in Tribenzoylphosphine. An Experimental Reinvestigation," *Tetrahedron Letters* 22:1983-1986, Pergamon Press Ltd., England (1979).
Macdonell, G.D., et al., "The Barrier to Carbon-Phosphorus Bond Rotation in Triaroylphosphines," *Tetrahedron Letters* 10:857-860, Pergamon Press, England (1978).
Micic, O.I., et al., "Synthesis and Characterization of InP Quantum Dots," *J. Phys. Chem.* 98:4966-4969, American Chemical Society, United States (1994).
Sawada, Y., et al., "TG-DTA-MS of Indium Acetate," *J. Mass Spectrom. Soc. Jpn.* 46(4):292-295, International Academic Publishing Company Ltd, Japan (1998).
Talapin, D.V., et al., "Etching of Colloidal InP Nanocrystals with Fluorides: Photochemical Nature of the Process Resulting in High Photoluminescence Efficiency," *J. Phys. Chem. B.* 106:12659-12663, American Chemical Society, United States (2002).
Wells, R.L., et al., "Use of Tris(trimethylsilyl)arsine to Prepare Gallium Arsenide and Indium Arsenide," *Chemistry of Materials* 1:4-6, American Chemical Society, United States (1989).
Xu, S., et al., "Rapid Synthesis of High-Quality InP Nanocrystals," *J. Am. Chem. Soc.* 128:1054-1055, American Chemical Society, United States (2006).
International Search Report for International Application No. PCT/US2016/061268, European Patent Office, Netherlands, dated Jan. 19, 2017, 2 pages.

*Primary Examiner* — Daniel C McCracken
(74) *Attorney, Agent, or Firm* — Sterne, Kessler, Goldstein & Fox P.L.L.C.

(57) ABSTRACT

The present invention is in the field of nanostructure synthesis. The present invention is directed to methods for producing nanostructures, particularly Group III-V semiconductor nanostructures. The present invention is also directed to preparing Group III inorganic compounds that can be used as precursors for nanostructure synthesis.

24 Claims, 12 Drawing Sheets

USE OF HETEROLEPTIC INDIUM HYDROXIDES AS PRECURSORS FOR INP NANOCRYSTALS

CROSS-REFERENCE TO RELATED APPLICATION

This application claims priority benefit of U.S. Provisional Application No. 62/255,121, filed Nov. 13, 2015, which is hereby incorporated by reference in its entirety.

FIELD OF THE INVENTION

The present invention is in the field of nanostructure synthesis. The present invention is directed to methods for producing nanostructures, particularly Group III-V semiconductor nanostructures. The present invention is also directed to preparing Group III inorganic compounds that can be used as precursors for nanostructure synthesis.

BACKGROUND OF THE INVENTION

Semiconductor nanostructures can be incorporated into a variety of electronic and optical devices such as photovoltaic devices and LEDs. The electrical and optical properties of these nanostructures vary depending on their composition, shape, and size. Group III-V semiconductors exhibit a number of desirable electrical properties such as low energy and direct band gap behaviors and high electron mobility, as well as other desirable properties such as thermal stability.

Methods for simply and reproducibly producing Group III-V semiconductor nanostructures—nanostructures of different sizes, shapes, and combinations thereof—are desirable. In some embodiments, the present invention provides such methods.

A traditional method for the synthesis of InP nanocrystals uses the commercially available precursor material $In(OAc)_3$ ($Ac=OCCH_3$). In a typical reaction, commercially available $In(OAc)_3$ is treated with a long-chain carboxylic acid in a reaction that removes acetic acid and forms a new material that is suitable for conversion to InP nanocrystals. Because $In(OAc)_3$ is both hydroscopic and moisture sensitive, it must be handled using inert atmosphere conditions requirements that increase production costs and require extensive purification of the other reagents used to remove any trace amounts of water.

Furthermore, upon exposure to moisture or humidity, $In(OAc)_3$ undergoes partial hydrolysis to form a mixture corresponding to the formula $In(OAc)_{3-n}(OH)_n$, wherein $0 \leq n \leq 1$. It has been found that many commercially available samples sold as "indium acetate" are actually mixtures having the formula $In(OAc)_{3-n}(OH)_n$.

Use of $In(OAc)_{3-n}(OH)_n$ in the typical synthesis of InP nanocrystals has several drawbacks. Firstly, since the reagent used is a mixture, the synthetic method will not produce consistent nanocrystal products. This is because a mixture will not allow one in the art to know and control the ratio of $In^{3+}$ to long-chain carboxylic acid. Secondly, treatment of $In(OAc)_{3-n}(OH)_n$ with long-chain carboxylic acids is expected to form $In(O_2C(CH_2)_mCH_3)_{3-n}(OH)_n$ upon ligand exchange. It is likely that $In(O_2C(CH_2)_mCH_3)_{3-n}(OH)_n$ is not suitable for nanocrystal growth due to the high sensitivity of the reaction kinetics. Thus, if $In(O_2C(CH_2)_mCH_3)_2(OH)$ and $In(O_2C(CH_2)_mCH_3)_3$ react at different rates, the precursor conversion in nanocrystal growth—a step that is critical for obtaining a narrow size distribution—will be more difficult to control than when a single reaction material is used. Therefore, if the value of n is not controlled, then the nanocrystal growth reaction may be irreproducible between batches.

Therefore, a need exists to identify a precursor material that not only can be handled in open air conditions without special treatment but also is stable for long periods of time and thus, allows the amount of indium used as a reagent to be precisely controlled.

SUMMARY OF THE INVENTION

The present invention provides a method for preparing a compound of formula I:

$$X_1\text{—}(O_2CCH_3)_2OH \qquad (I)$$

wherein $X_1$ is B, Al, Ga, In, or Tl;
the method comprising:
(1) reacting:

$$X_1\text{—}(O_2CCH_3)_{3-n}(OH)_n$$

wherein $0 < n \leq 1$; with an organic solvent and water; and
(2) drying at a temperature between about 10° C. and about 80° C.

In some embodiments, $0 < n < 1$.

In some embodiments, the organic solvent is selected from the group consisting of methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, diethyl ether, dibutyl ether, cyclopentyl methyl ether, anisole, toluene, xylene, heptanes, and mixtures thereof. In some embodiments, the organic solvent is diethyl ether.

In some embodiments, the drying is under vacuum.

In some embodiments, the drying is at a temperature between about 20° C. and about 60° C. In some embodiments, the drying is at a temperature between about 30° C. and about 50° C. In some embodiments, the drying is at a temperature between about 35° C. and about 45° C.

In some embodiments, in the compound of formula (I), $X_1$ is In.

In some embodiments, the drying is for a time between about 1 hour and about 20 hours. In some embodiments, the drying is for a time between about 1 hour and about 15 hours.

In some embodiments, in the compound of formula (III), $X_1$ is In, the organic solvent is diethyl ether, the temperature is between about 35° C. and about 45° C., and the drying is for a time between about 1 hour and about about 15 hours.

The present invention provides a method of preparing a compound of formula III:

$$X_1\text{—}(O_2C(CH_2)_bCH_3)_{3-c}(OH)_c \qquad (III)$$

wherein:
$X_1$ is B, Al, Ga, In, or Tl;
b is between 7 and 19; and
c is 1 or 2;
the method comprising reacting:
(1) a compound of formula IV:

$$X_1\text{—}(OH)_a(O_2CCH_3)_{3-a} \qquad (IV)$$

wherein:
$X_1$ is B, Al, Ga, In, or Tl; and
a is 1 or 2;

(2) with a compound of formula V:

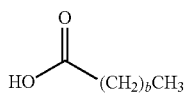

wherein:
b is between 7 and 19.

In some embodiments, in the compound of formula (III), $X_1$ is In.

In some embodiments, in the compound of formula (III), c is 2.

In some embodiments, in the compound of formula (III), b is between 7 and 12. In some embodiments, in the compound of formula (III), b is 10.

In some embodiments, the reacting occurs at a first temperature between about 20° C. to about 100° C. In some embodiments, the reacting occurs at a second temperature between about 60° C. to about 200° C.

In some embodiments, the molar ratio of the compound of formula (IV) to the compound of formula (V) is between about 1:2.0 to about 1:2.8.

In some embodiments, the molar ratio of the compound of formula (IV) to the compound of formula (V) is between about 1:2.0 to about 1:2.3. In some embodiments, the molar ratio of the compound of formula (IV) to the compound of formula (V) is between about 1:2.0 to about 1:2.2.

In some embodiments, $X_1$ is In, b is 10, c is 2, and the molar ratio of the compound of formula (IV) to the compound of formula (V) is between about 1:2.0 to about 1:2.2.

The present invention provides a method for production of a Group III-V nanostructure, the method comprising:
(a) providing a Group III precursor, wherein the Group III precursor is a compound of formula (III):

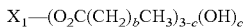

wherein:
$X_1$ is B, Al, Ga, In, or Tl;
b is between 7 and 19; and
c is 1 or 2;
(b) providing a Group V precursor comprising a Group V atom; and
(c) reacting the Group III and the Group V precursor to produce the nanostructure.

In some embodiments, in the compound of formula (III), $X_1$ is In.

In some embodiments, in the compound of formula (III), c is 2.

In some embodiments, in the compound of formula (III), b is between 7 and 12. In some embodiments, in the compound of formula (III), b is 10.

In some embodiments, in the compound of formula (III), $X_1$ is In, c is 2, and b is 10.

In some embodiments, the Group V precursor comprises a Group V atom substituted with an acyl group. In some embodiments, the Group V precursor is a triacylphosphine.

In some embodiments, the Group V precursor comprises a Group V atom substituted with three unsaturated groups. In some embodiments, the Group V precursor comprises a tris(trialkylsilyl) substituted Group V atom. In some embodiments, the Group V precursor is tris(trimethylsilyl) phosphine.

The present invention provides a composition comprising: a Group V precursor comprising a Group V atom; a Group III precursor, wherein the Group III precursor is a compound of formula (III):

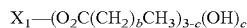

wherein:
$X_1$ is B, Al, Ga, In, or Tl;
b is between 7 and 19; and
c is 1 or 2; and
one or more nanostructures comprising the Group III atom and the Group V atom.

In some embodiments, the Group V precursor comprises a tris(trialkylsilyl) substituted Group V atom. In some embodiments, the Group V precursor is tris(trimethylsilyl) phosphine.

In some embodiments, in the compound of formula (III), $X_1$ is In.

In some embodiments, in the compound of formula (III), c is 2.

In some embodiments, in the compound of formula (III), b is between 7 and 12. In some embodiments, b is 10.

In some embodiments, in the compound of formula (III), $X_1$ is In, c is 2, and b is 10.

DEFINITIONS

Figure 1:
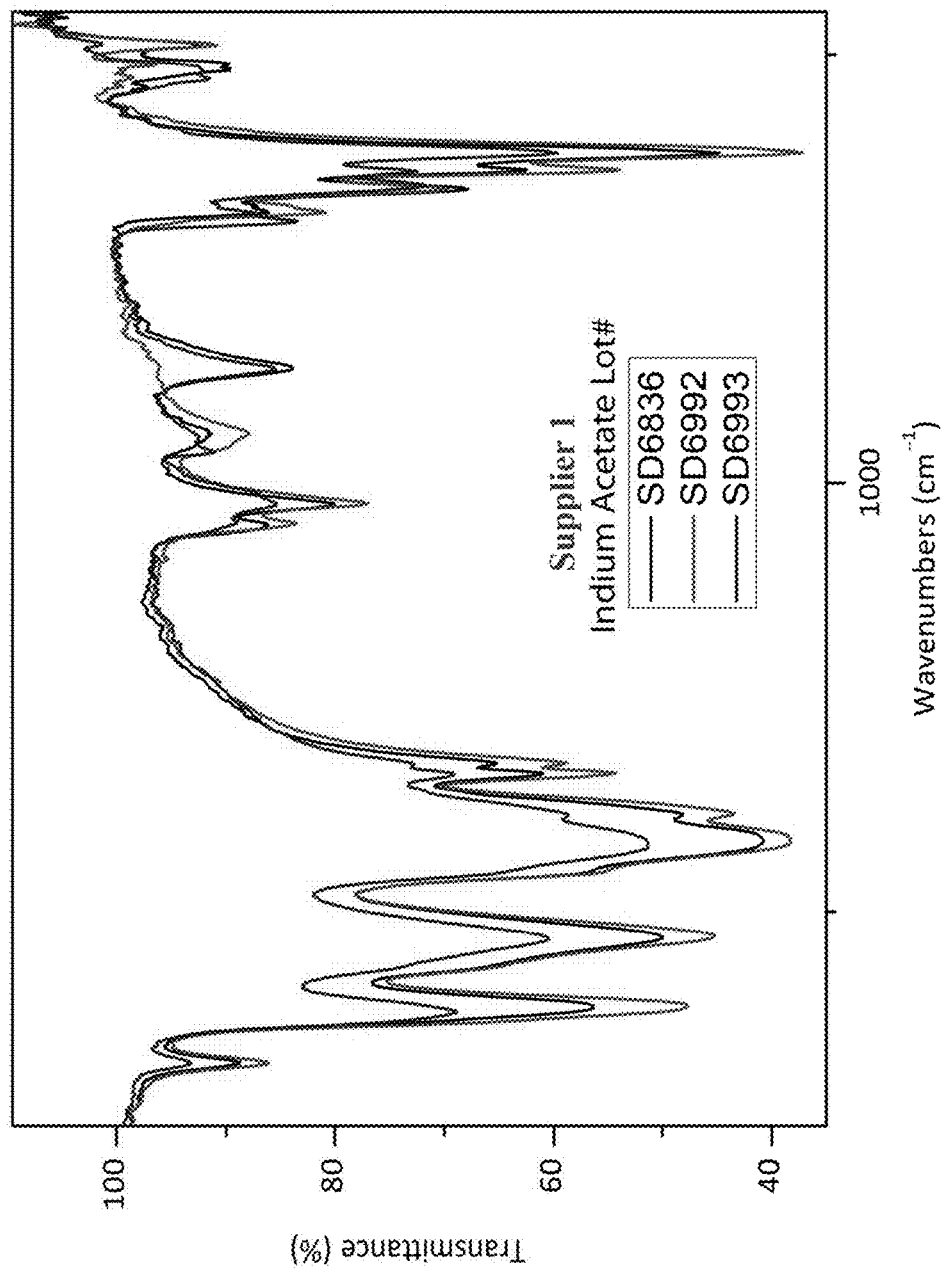
FIG. 1 is a fourier transform infrared (FTIR) spectrum of three lots of indium acetate material purchased from a single commercial supplier. As shown, the spectrum for all three lots are consistent.
Figure 2:
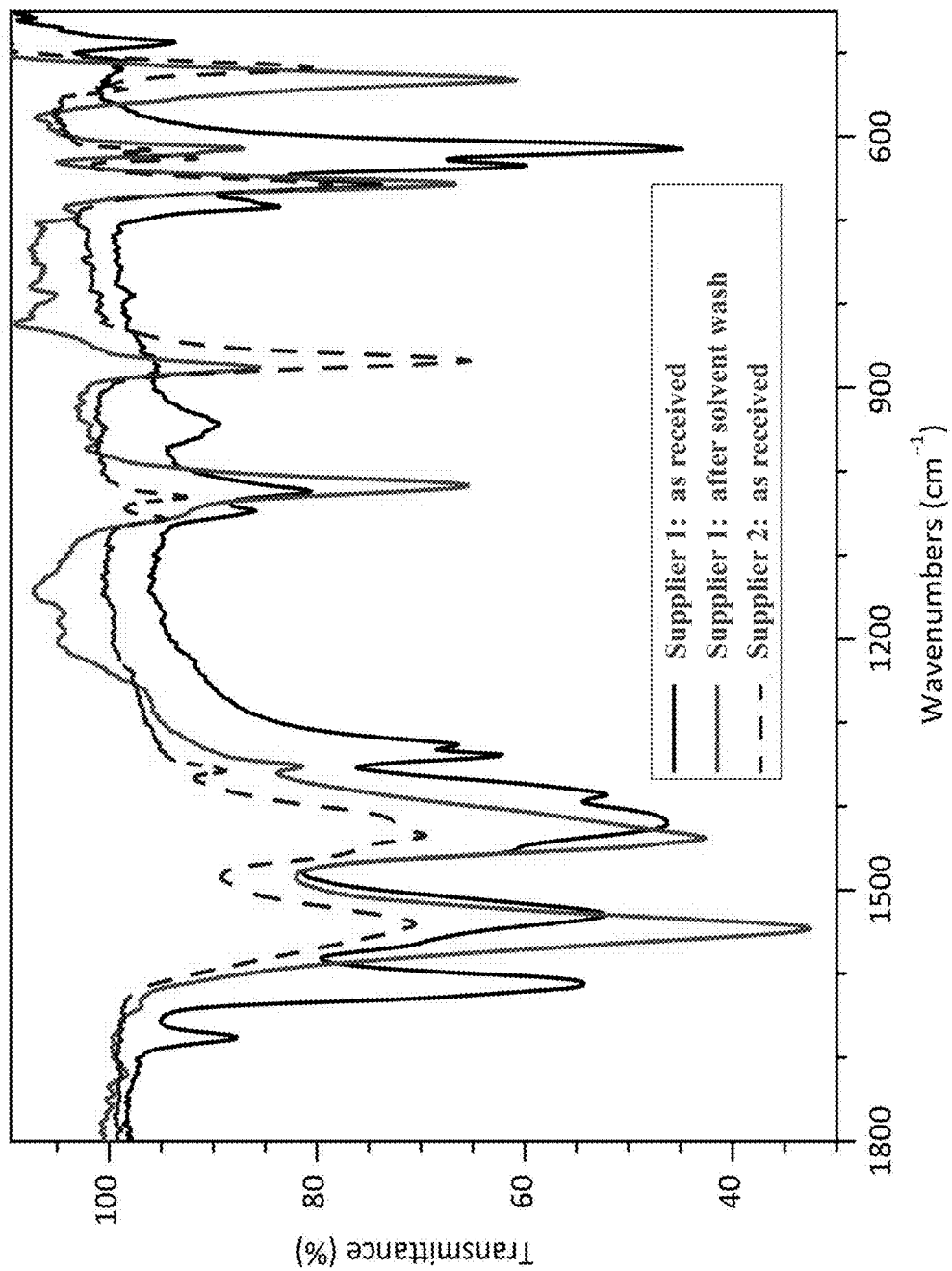
FIG. 2 is a FTIR spectrum of lots of indium acetate from two different commercial suppliers. After washing the lot from the first supplier with methanol and hexanes, several bands disappeared in the spectrum and 30% of the mass was lost.
Figure 3:
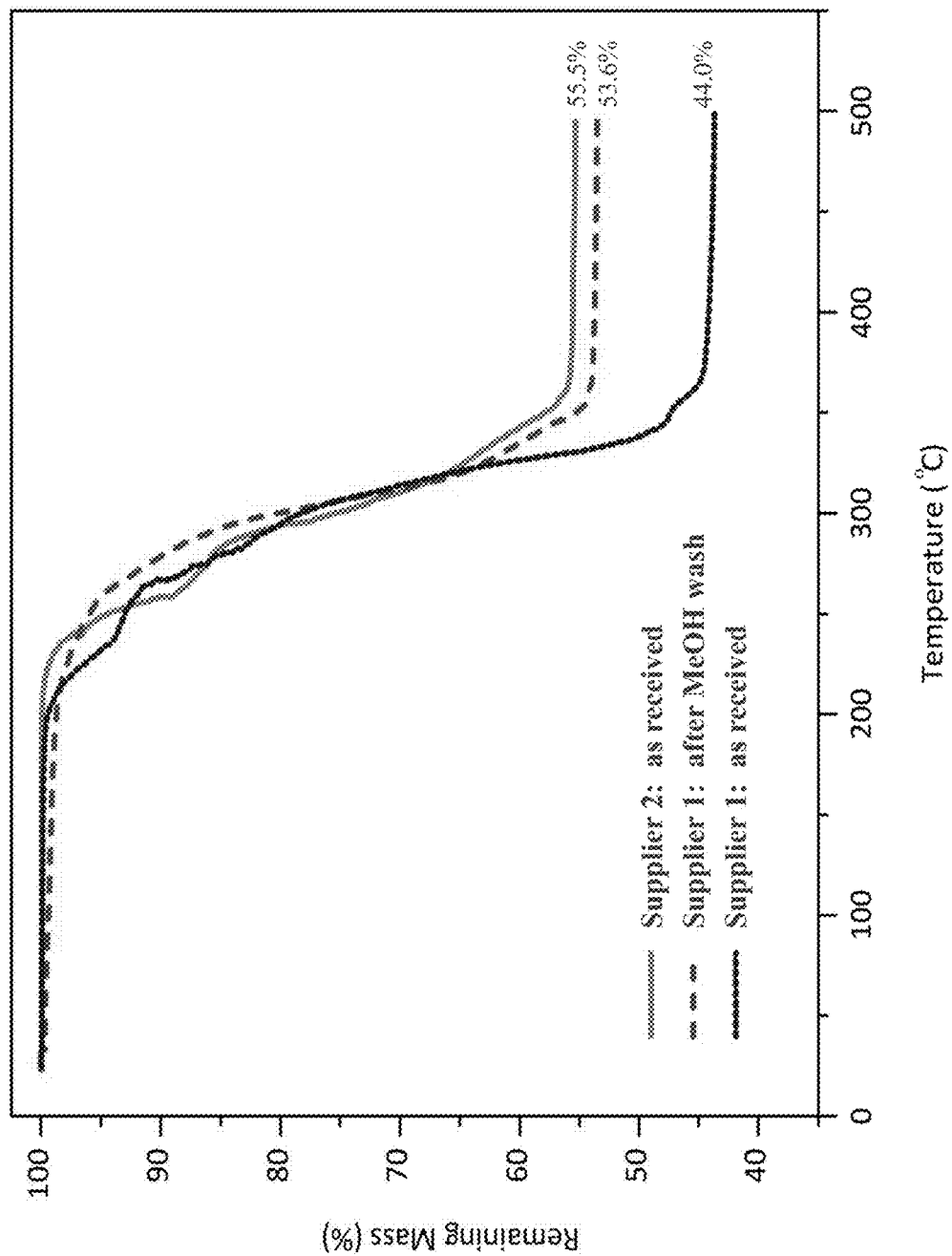
FIG. 3 is a graph of the mass of indium acetate lots as temperature increases. After washing the lot from the first supplier with methanol and hexanes, the sample shows a mass consistent with $In(OOCCH_3)_2OH$.
Figure 4:
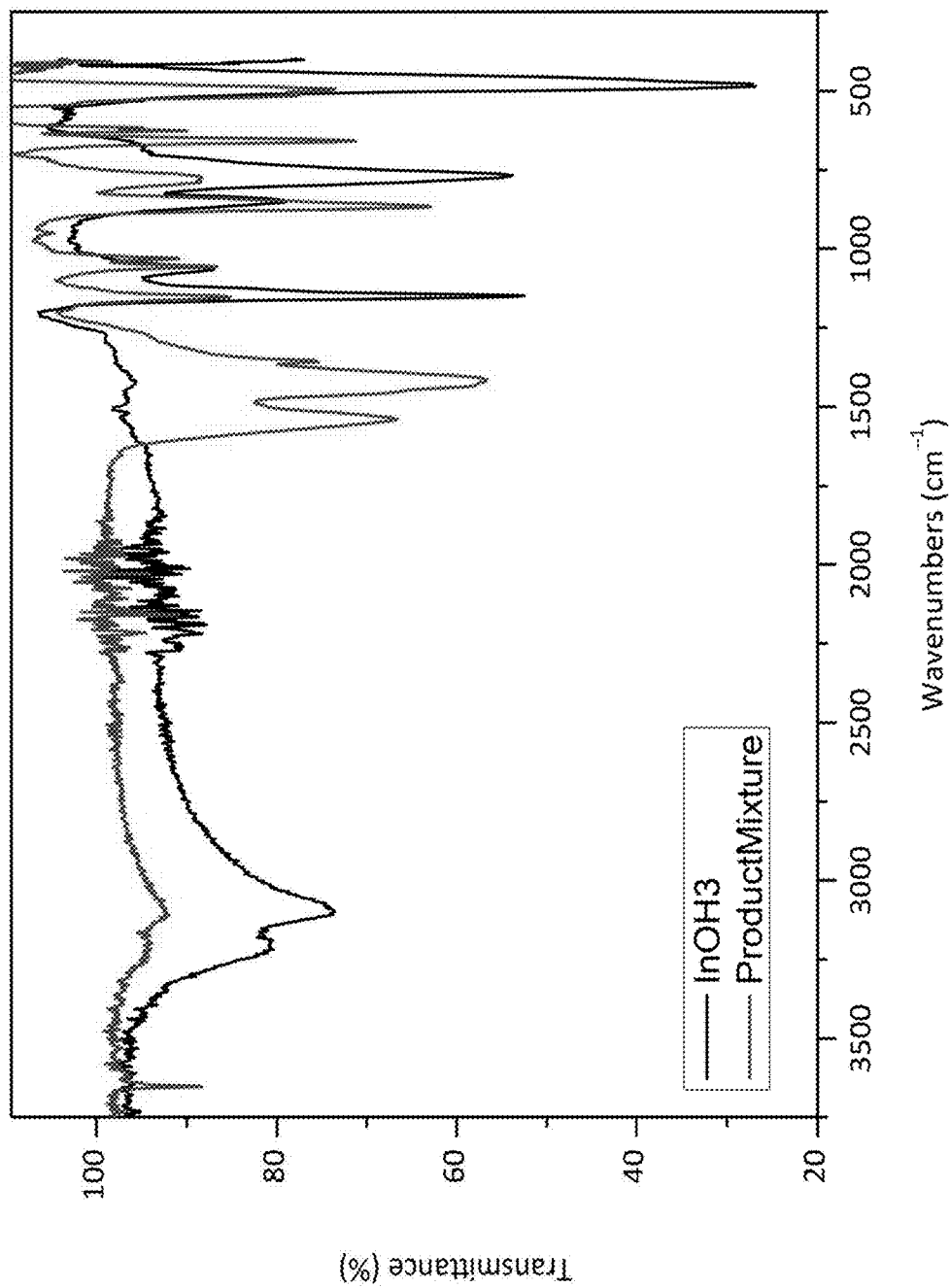
FIG. 4 is a FTIR of an incomplete reaction product of $CH_3COOH$ with $In(OH)_3$.
Figure 5:
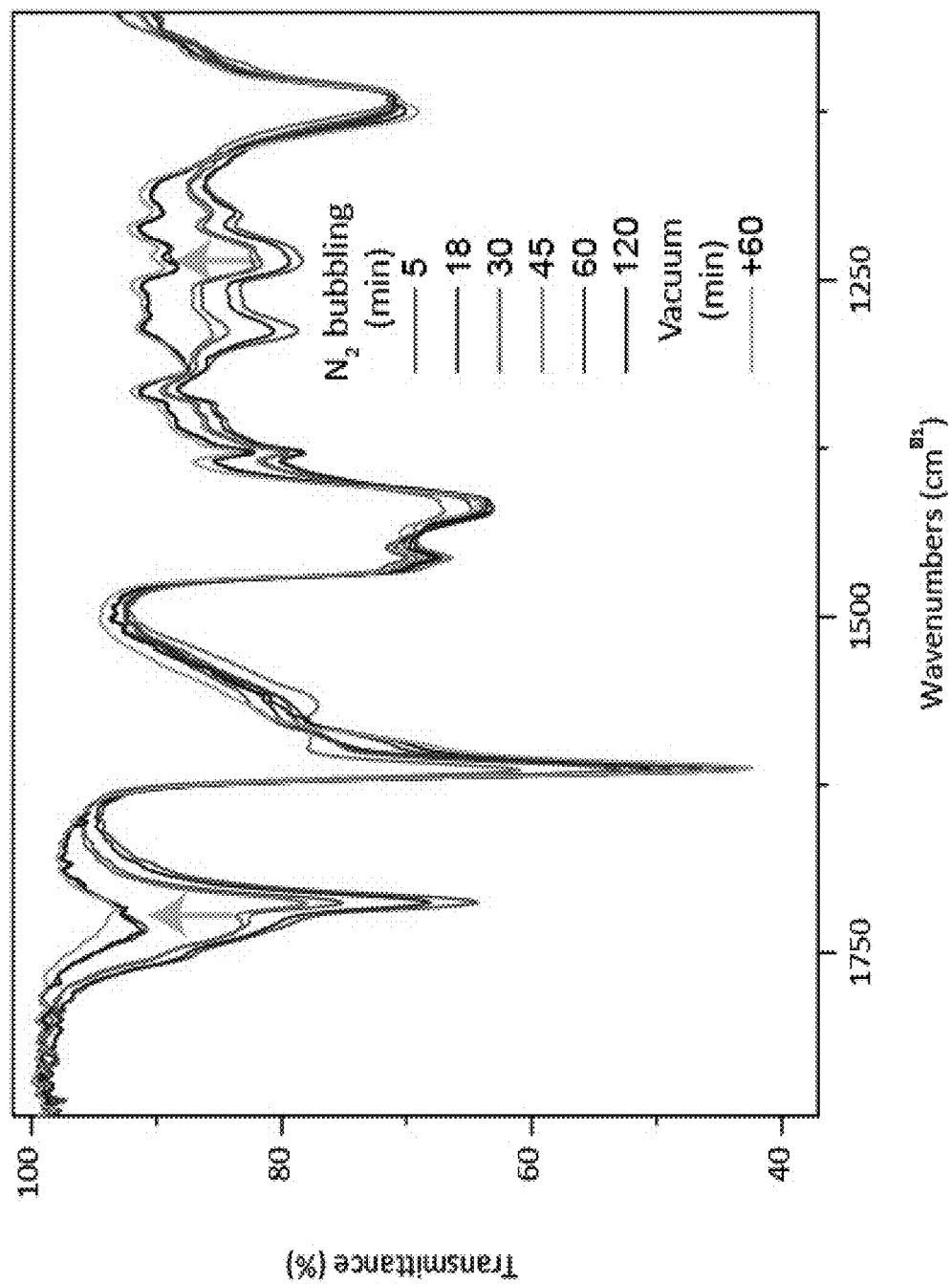
FIG. 5 is a FTIR spectrum monitoring carboxylate exchange. The two arrows on the spectrum indicate that two characteristic bands disappear over the course of ligand exchange.
Figure 6:
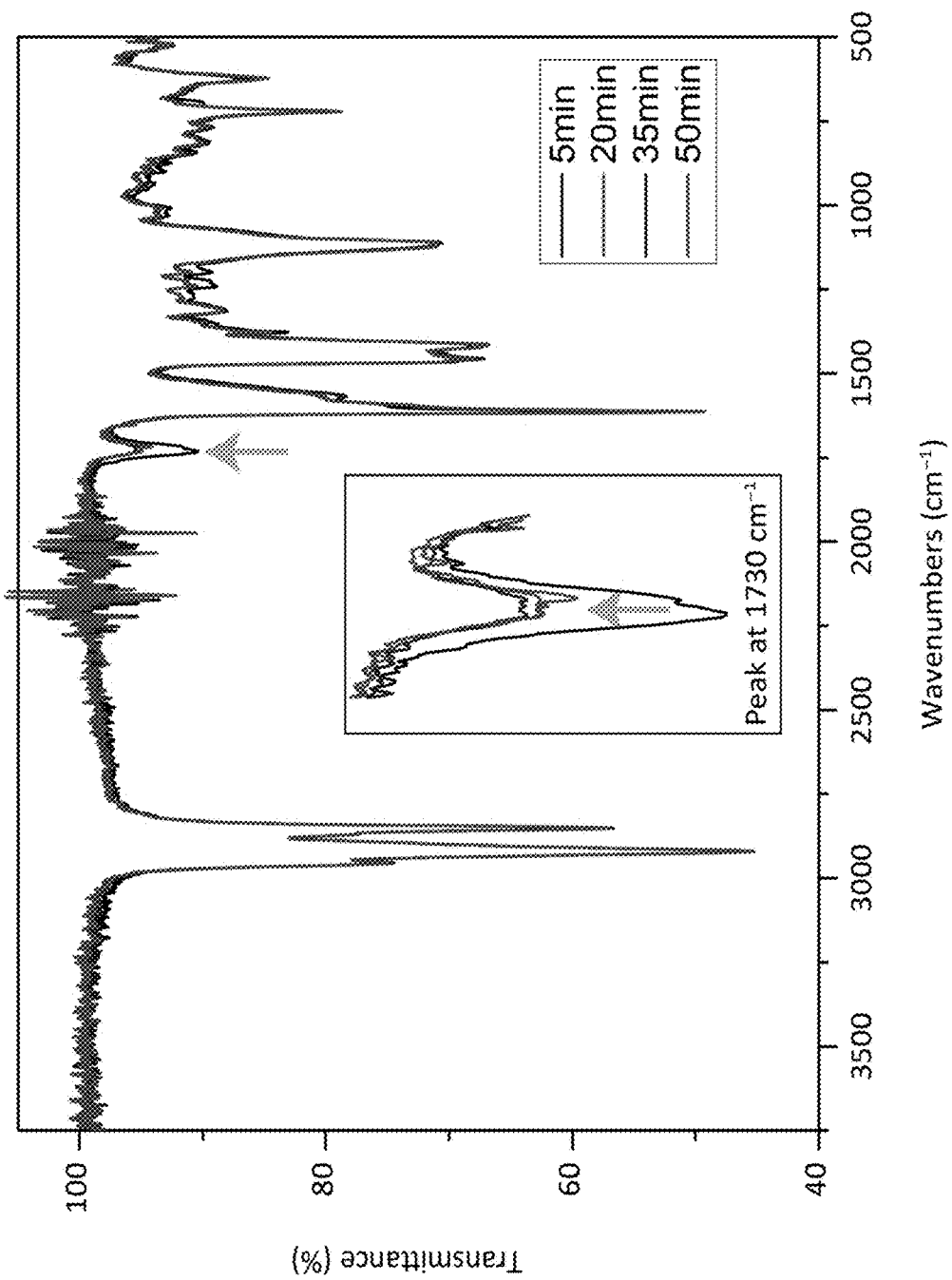
FIG. 6 is a FTIR spectrum of purified $In(OOCCH_3)_2OH$ reacted with lauric acid with nitrogen sparging. Treatment of $In(OOCCH_3)_2OH$ with lauric acid produces a strong band at 1625 cm$^{-1}$ with the disappearance of the band at 1730 cm$^{-1}$.
Figure 7:
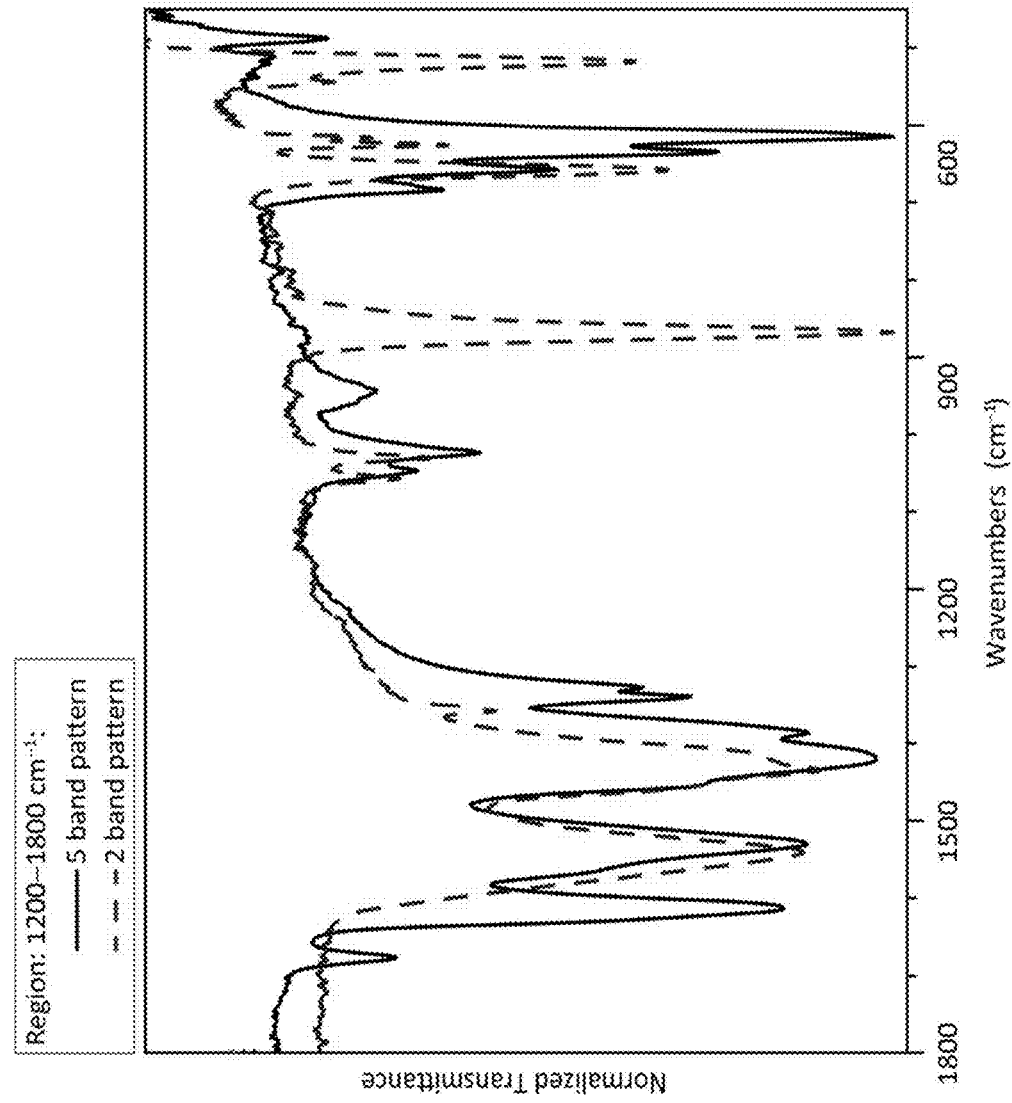
FIG. 7 is a FTIR spectrum of commercial indium acetate starting material before hydrolysis which shows a 5-band pattern and after hydrolysis which shows a 2-band pattern consistent with $In(OOCCH_3)_2OH$.
Figure 8:
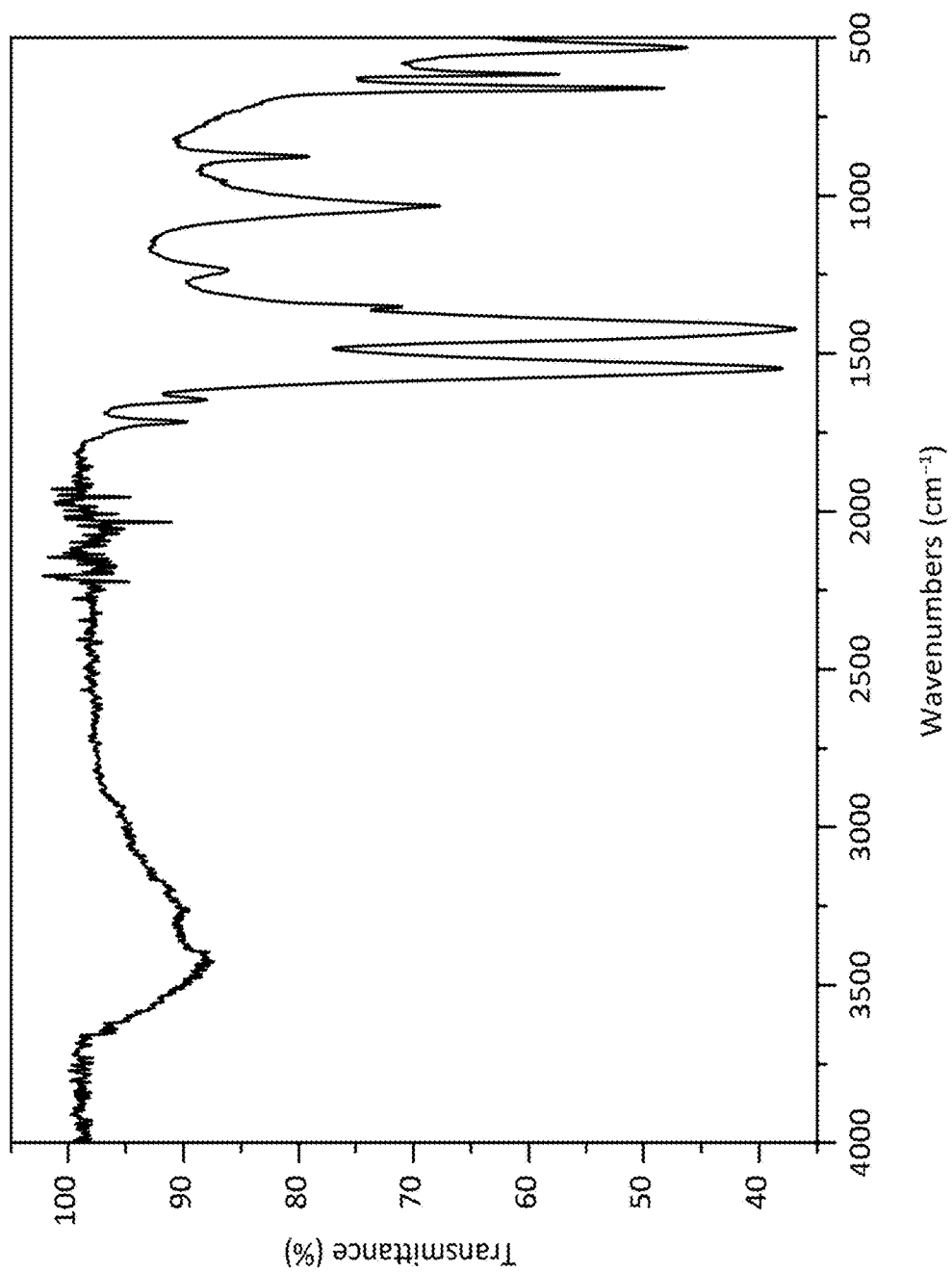
FIG. 8 is a FTIR spectrum of a 35 g sample of commercial indium acetate material after hydrolysis in diethyl ether. The hydrolyzed material shows a 2-band pattern; however, after vacuum drying at 20° C. overnight, a broad band at 2800 cm$^{-1}$ still remains.
Figure 9:
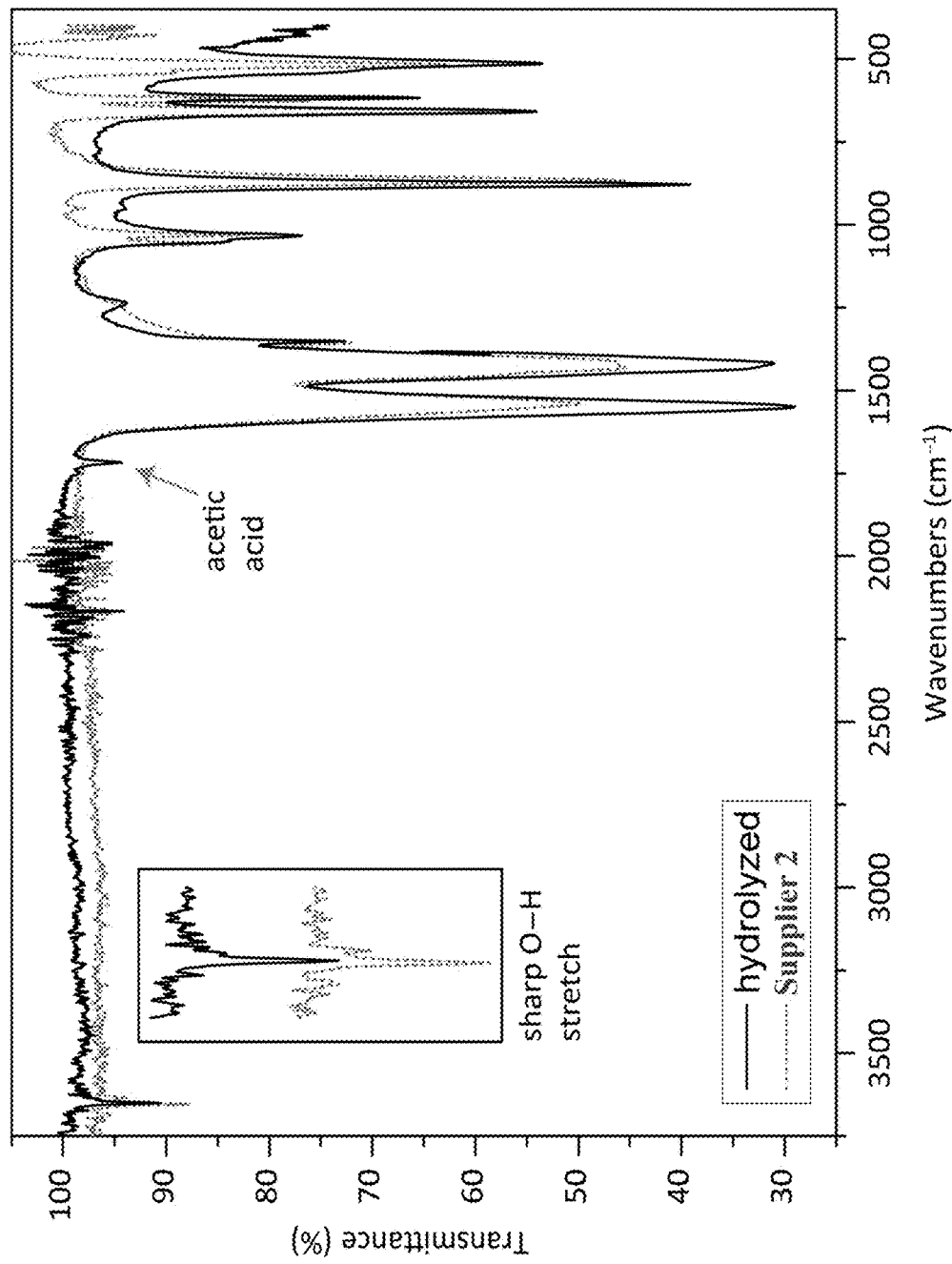
FIG. 9 is a FTIR spectrum of a 35 g sample of commercial indium acetate after hydrolysis in diethyl ether. After vacuum drying at 40° C. overnight, a sharp O—H stretch is present and there is no broad band at 2800 cm$^{-1}$.
Figure 10:
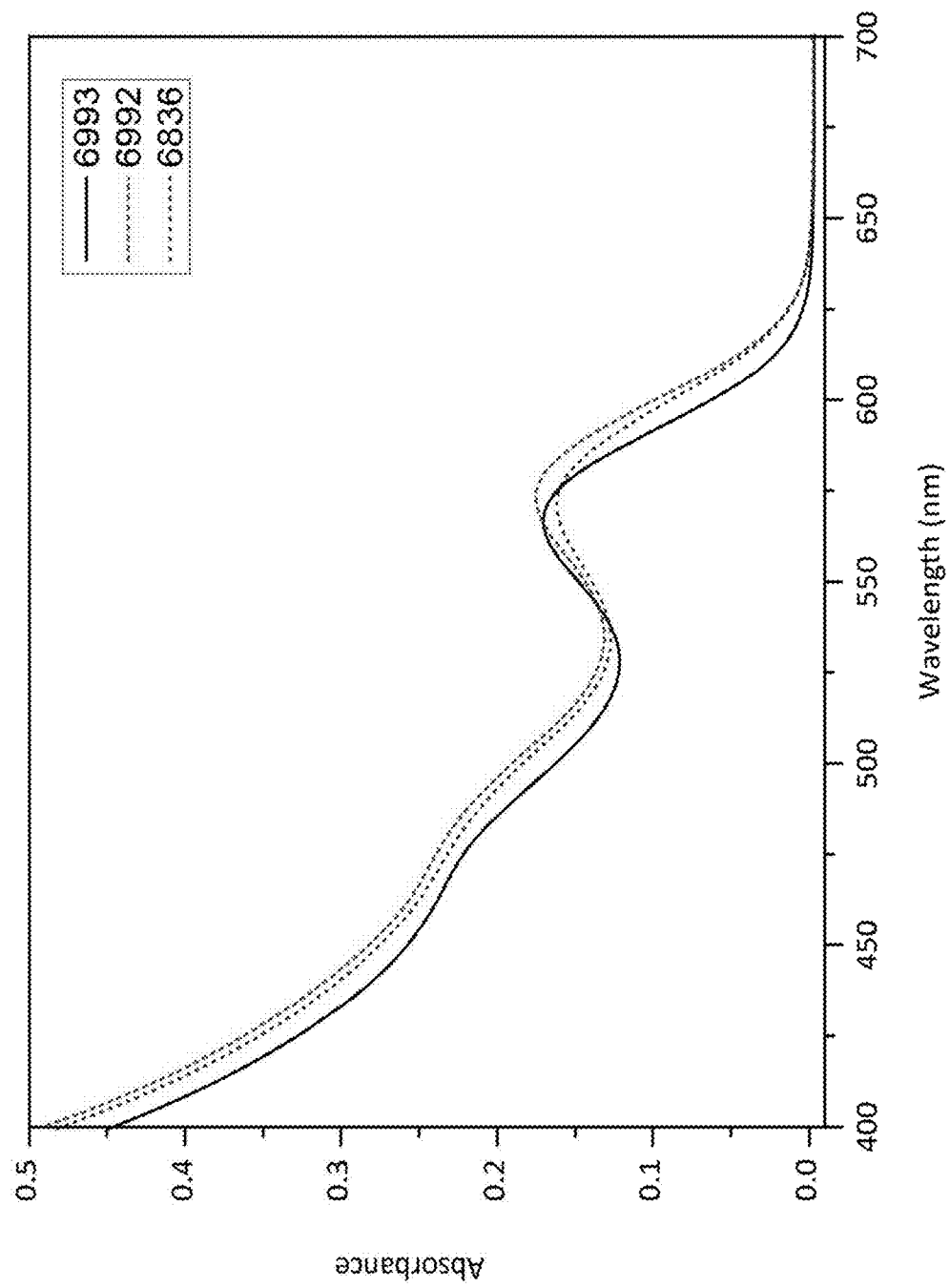
FIG. 10 is an overlay of three UV-Vis spectra of InP nanoparticles prepared from three lots of commercial indium acetate that had been subject to hydrolysis to produce In(OOCCH$_3$)$_2$OH prior to reaction with 2.6 equivalents of lauric acid and tris(trimethylsilyl) phosphine.
Figure 11:
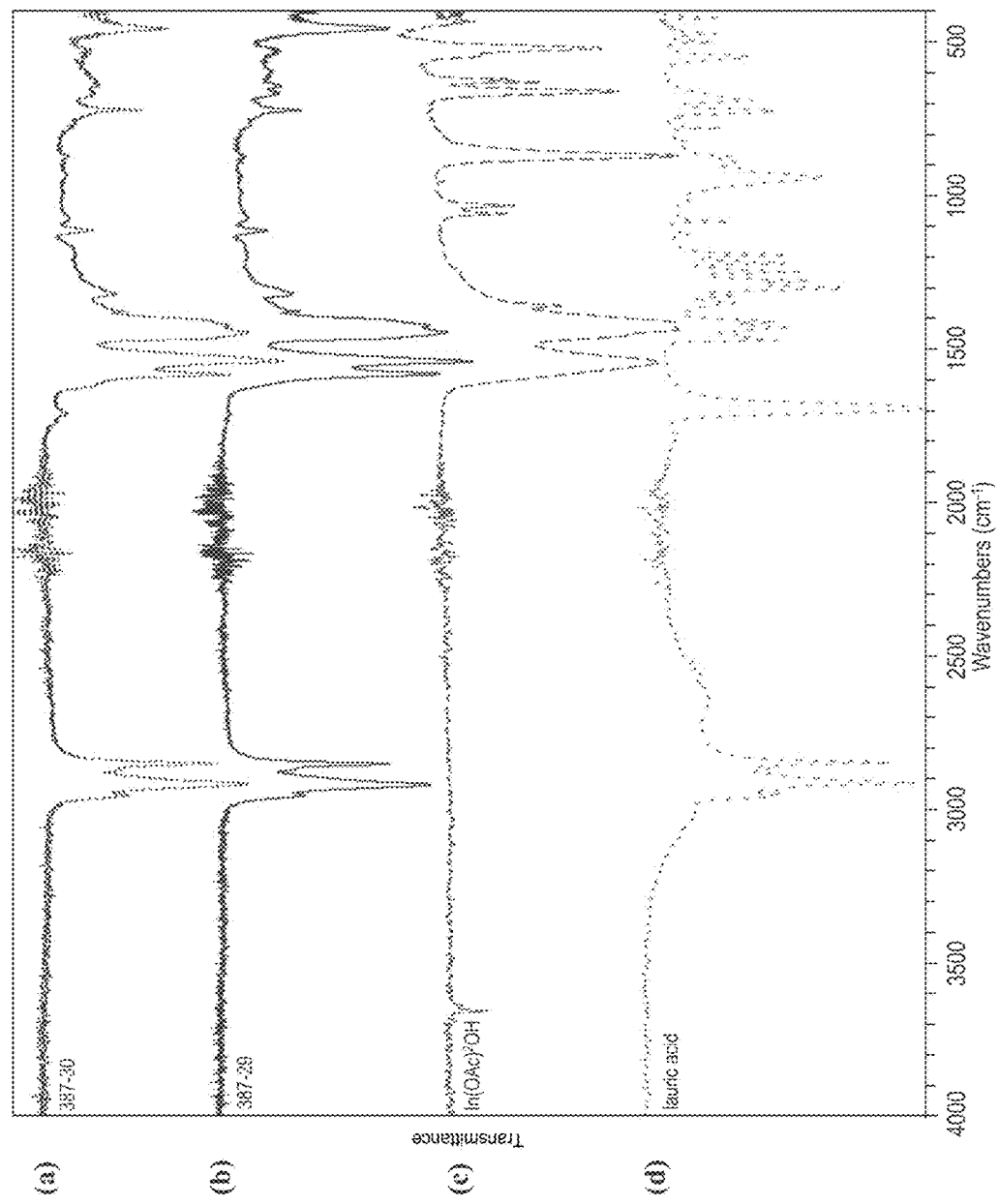
FIG. 11 are superimposed FTIR spectra of In(OOC(CH$_2$)$_{10}$CH$_3$)$_2$OH produced using (a) 3.15 equivalent of lauric acid and (b) 2.15 equivalents of lauric acid. The FTIR spectra of (c) the In(OOCCH$_3$)$_2$OH starting material and (d) lauric acid are also shown. As shown in (a), the product of the reaction using 3.15 equivalents of lauric acid contains free lauric acid.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, exemplary materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a nanostructure" includes a plurality of such nanostructures, and the like.

The term "about" as used herein indicates the value of a given quantity varies by +/−10% of the value, or optionally +/−5% of the value, or in some embodiments, by +/−1% of the value so described.

An "acyl group" has the formula RC(O)—, where R is an organic group. The acyl group can be, e.g., substituted or unsubstituted. In a "substituted acyl group", at least one hydrogen in the organic group is replaced with one or more other atoms.

An "alkenyl group" refers to a linear, branched, or cyclic unsaturated hydrocarbon moiety that comprises one or more carbon-carbon double bonds. Alkenyl groups can be substituted or unsubstituted.

An "alkyl group" refers to a straight or branched, saturated, aliphatic radical having the number of carbon atoms indicated. In some embodiments, the alkyl is C$_{1-2}$ alkyl, C$_{1-3}$ alkyl, C$_{1-4}$ alkyl, C$_{1-5}$ alkyl, C$_{1-6}$ alkyl, C$_{1-7}$ alkyl, C$_{1-8}$ alkyl, C$_{1-9}$ alkyl, C$_{1-10}$ alkyl, C$_{1-12}$ alkyl, C$_{1-14}$ alkyl, C$_{1-16}$ alkyl, C$_{1-18}$ alkyl, C$_{1-20}$ alkyl, C$_{8-20}$ alkyl, C$_{12-20}$ alkyl, C$_{14-20}$ alkyl, C$_{16-20}$ alkyl, or C$_{18-20}$ alkyl. For example, C$_{1-6}$ alkyl includes, but is not limited to, methyl, ethyl, propyl, isopropyl, butyl, isobutyl, sec-butyl, tert-butyl, pentyl, isopentyl, and hexyl. In some embodiments, the alkyl is octyl, nonyl, decyl, undecyl, dodecyl, tridecyl, tetradecyl, pentadecyl, hexadecyl, heptadecyl, octadecyl, nonadecyl, or icosyl. In some embodiments, the alkyl group is substituted. In some embodiments, the alkyl group is unsubstituted.

A "long-chain alkyl group" is an alkyl groups, as defined above, having at least 8 carbon chain atoms. In some embodiments, the long-chain alkyl group is C$_{8-20}$ alkyl, C$_{12-20}$ alkyl, C$_{14-20}$ alkyl, C$_{16-20}$ alkyl, or C$_{18-20}$ alkyl. In some embodiments, the long-chain alkyl group is octyl, nonyl, decyl, undecyl, dodecyl, tridecyl, tetradecyl, pentadecyl, hexadecyl, heptadecyl, octadecyl, nonadecyl, or icosyl. In some embodiments, the long-chain alkyl group is substituted with a silane group.

An "unbranched alkyl group" is a linear, n-alkyl group.

An "unsubstituted alkyl group" has the formula —(CH$_2$)$_n$CH$_3$, where n is greater than or equal to zero. In a "substituted alkyl group", at least one hydrogen is replaced with one or more other atoms. For example, at least one hydrogen can be replaced with a moiety containing one or more carbon, oxygen, sulfur, nitrogen, or halogen atoms. An alkyl group can, e.g., be branched or unbranched.

An "unsaturated group" contains at least one element of unsaturation. An "element of unsaturation" is a double bond (of any type), a triple bond (of any type), or a ring.

An "alkynyl group" refers to a linear, branched, or cyclic unsaturated hydrocarbon moiety that comprises one or more carbon-carbon triple bonds. Alkynyl groups can be substituted or unsubstituted.

An "alkyl amine" is an amine having at least one alkyl substituent on the nitrogen atom. A "monoalkyl amine" contains one alkyl group on the nitrogen, a "bialkyl amine" contains two alkyl groups on the nitrogen, and a "trialkyl amine" contains three alkyl groups on the nitrogen.

The term "alkyl-aryl group" refers to a group that comprises alkyl and aryl moieties.

The term "aryl group" refers to a chemical substituent comprising or consisting of an aromatic group. Exemplary aryl groups include, e.g., phenyl groups, benzyl groups, tolyl groups, xylyl groups, alkyl-aryl groups, or the like. Aryl groups optionally include multiple aromatic rings (e.g., diphenyl groups, etc.). The aryl group can be, e.g., substituted or unsubstituted. In a "substituted aryl group", at least one hydrogen is replaced with one or more other atoms.

An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

A "branched nanostructure" is a nanostructure having three or more arms, where each arm has the characteristics of a nanorod, or a nanostructure having two or more arms, each arm having the characteristics of a nanorod and emanating from a central region that has a crystal structure distinct from that of the arms. Examples include, but are not limited to, bipods, tripods, and nanotetrapods (tetrapods).

Two atoms are "bonded to" each other when they share a chemical bond, e.g., a covalent bond, a polar covalent bond, or an ionic bond.

A "by-product" or "co-product" of a nanostructure synthesis reaction is a product produced in addition to the desired nanostructure.

A "carboxamide group" has the formula —C(O)NRR', where R and R' are independently selected organic groups (e.g., an alkyl or aryl group).

"Cp" represents cyclopentadiene or an unsubstituted cyclopentadienyl group, as will be clear from the context. A cyclopentadienyl group can be, e.g., substituted or unsubstituted. In a "substituted cyclopentadienyl group", at least one hydrogen is replaced with one or more other atoms.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The "diameter of a nanocrystal" refers to the diameter of a cross-section normal to a first axis of the nanocrystal, where the first axis has the greatest difference in length with respect to the second and third axes (the second and third axes are the two axes whose lengths most nearly equal each other). The first axis is not necessarily the longest axis of the nanocrystal; e.g., for a disk-shaped nanocrystal, the cross-section would be a substantially circular cross-section normal to the short longitudinal axis of the disk. Where the cross-section is not circular, the diameter is the average of the major and minor axes of that cross-section.

The "diameter of a nanorod" refers to the diameter of a cross-section normal to the major principle axis (the long axis) of the nanorod. Where the cross-section is not circular, the diameter is the average of the major and minor axes of that cross-section.

An "ester" has the formula RC(O)OR', where R and R' are independently selected organic groups (e.g., an alkyl or aryl group).

An "ether" comprises two carbon atoms attached to a single oxygen atom.

A "furyl group" comprises a furan ring.

A "furfuryl group" is an acyl group comprising a furan ring (e.g., furan-2-carboxaldehyde).

A "ketone" comprises two carbon atoms attached to a single carbonyl group.

A "Group III atom" is an atom selected from Group III of the periodic table of the elements. Examples include, but are not limited to, B, Al, Ga, In, and Tl.

A "Group V atom" is an atom selected from Group V of the periodic table of the elements. Examples include, but are not limited to, N, P, As, Sb, and Bi.

A "Group V organometallic compound" contains a Group V atom directly bonded to at least one carbon atom.

The term "Group III-V semiconductor" refers to a semiconductor containing at least one Group III atom and at least one Group V atom. Typically, a Group III-V semiconductor includes one Group III and one Group V atom; examples include, but are not limited to, InN, InP, InAs, InSb, GaN, GaP, GaAs, GaSb, AlN, AlP, AlAs, or AlSb.

A "heteroatom" refers to any atom which is not a carbon or hydrogen atom. Examples include, but are not limited to, oxygen, nitrogen, sulfur, phosphorus, and boron.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm. In some embodiments, the nanocrystal has a dimension of less than about 200 nm, less than about 100 nm, less than about 50 nm, less than about 20 nm, or less than about 10 nm. The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. In some embodiments, each of the three dimensions of the nanocrystal has a dimension of less than about 500 nm, less than about 200 nm, less than about 100 nm, less than about 50 nm, less than about 20 nm, or less than about 10 nm. Examples of nanocrystals include, but are not limited to, substantially spherical nanocrystals, branched nanocrystals, and substantially monocrystalline nanowires, nanorods, nanodots, quantum dots, nanotetrapods, tripods, bipods, and branched tetrapods (e.g., inorganic dendrimers).

A "substantially spherical nanocrystal" is a nanocrystal with an aspect ratio between about 0.8 and about 1.2.

A "nanorod" is a nanostructure that has one principle axis that is longer than the other two principle axes. Consequently, the nanorod has an aspect ratio greater than one. Nanorods of this invention typically have an aspect ratio between about 1.5 and about 10, but can have an aspect ratio greater than about 10, greater than about 20, greater than about 50, greater than about 100, or greater than about 10,000. Longer nanorods (e.g., those with an aspect ratio greater than about 10) are sometimes referred to as nanowires. The diameter of a nanorod is typically less than about 500 nm, less than about 200 nm, less than about 150 nm, less than about 100 nm, less than about 50 nm, less than about 25 nm, less than about 10 nm, or less than about 5 nm. Nanorods can have a variable diameter or can have a substantially uniform diameter, that is, a diameter that shows a variance less than about 20%, less than about 10%, less than about 5%, or less than about 1% over the region of greatest variability. Nanorods are typically substantially crystalline and/or substantially monocrystalline, but can be, e.g., polycrystalline or amorphous.

A "nanostructure" is a structure having at least one region or characteristic dimension with a dimension of less than about 500 nm, less than about 200 nm, less than about 100 nm, less than about 50 nm, or less than about 20 nm. Typically, the region or characteristic dimension will be along the smallest axis of the structure. Examples of such structures include nanowires, nanorods, nanotubes, branched nanostructures, nanotetrapods, tripods, bipods, nanocrystals, nanodots, quantum dots, nanoparticles, and the like. Nanostructures can be, e.g., substantially crystalline, substantially monocrystalline, polycrystalline, amorphous, or a combination thereof. In one aspect, each of the three dimensions of the nanostructure has a dimension of less than about 500 nm, less than about 200 nm, less than about 100 nm, or less than about 50 nm, or less than about 20 nm.

A "nanotetrapod" is a generally tetrahedral branched nanostructure having four arms emanating from a central region or core, where the angle between any two arms is approximately 109.5 degrees. Typically, the core has one crystal structure and the arms have another crystal structure.

A "phosphine" has the formula PRR'R", where R, R', and R" are independently an alkyl group, acyl group, aryl group (e.g., alkylaryl group), alkenyl group, alkynyl group, ester group, hydrogen, halide, or the like.

A "tri-n-alkyl phosphine" has the formula $PR_3$, where R is an n-alkyl group.

A "phosphinic acid" has the formula RR'P(O)OH, where R and R' are independently any organic group (e.g., any alkyl or aryl group) or hydrogen. A "phosphinate moiety" thus has the formula RR'P(O)O—.

A "phosphonic acid" has the formula $RP(O)(OH)_2$ or RP(O)(OR')(OH), where R and R' are independently an organic group (e.g., an alkyl or aryl group). A "phosphonate moiety" thus has the formula RP(O)(OH)O— or RP(O)(OR')O—.

A "carboxylic acid" has the formula RC(O)OH, where R is an organic group (e.g., an alkyl group or an aryl group). A "carboxylate moiety" thus has the formula RC(O)O—.

A "boronic acid" has the formula $RB(OH)_2$, where R is an organic group (e.g., an alkyl or aryl group) or hydrogen.

A "sulfonic acid" has the formula $RS(O)_2OH$, where R is an organic group (e.g., an alkyl or aryl group) or hydrogen.

A "precursor" in a nanostructure synthesis reaction is a chemical substance (e.g., a compound or element) that reacts, e.g., with another precursor, and thereby contributes at least one atom to the nanostructure produced by the reaction.

A "surfactant" is a molecule capable of interacting (whether weakly or strongly) with one or more faces of a nanostructure and/or with one or more precursors used in producing the nanostructure.

A "non-coordinating solvent" is one that does not interact with one or more faces of a nanostructure and/or with one or more precursors used in producing the nanostructure. A typical weakly binding surfactant comprises a heteroatom having a free (non-bonded within the surfactant) pair of electrons, while a typical non-coordinating solvent does not include such a heteroatom and free pair of electrons.

A "trisubstituted Group V atom" is a Group V atom that is directly bonded to three other atoms. The three other atoms can be identical or distinct. Each of the three other atoms is optionally part of a chemical group.

A "triacyl substituted Group V atom" is a Group V atom that is bonded to three identical acyl groups. The acyl group can be, e.g., substituted or unsubstituted.

A "trialkyl substituted Group V atom" is a Group V atom that is bonded to three identical alkyl groups. The alkyl group can be, e.g., unbranched or branched and/or substituted or unsubstituted.

A "triaryl substituted Group V atom" is a Group V atom that is bonded to three identical aryl groups. The aryl group can be, e.g., substituted or unsubstituted.

An "alkyl group" refers to a linear, branched, or cyclic saturated hydrocarbon moiety and includes all positional isomers. Alkyl groups can be, e.g., substituted or unsubstituted.

An "unbranched alkyl group" is a linear, n-alkyl group.

An "unsubstituted alkyl group" has the formula $—(CH_2)_nCH_3$, where n is greater than or equal to zero. In a "substituted alkyl group", at least one hydrogen is replaced with one or more other atoms. For example, at least one hydrogen can be replaced with a moiety containing one or more carbon, oxygen, sulfur, nitrogen, or halogen atoms. An alkyl group can, e.g., be branched or unbranched.

An "unsaturated group" contains at least one element of unsaturation. An "element of unsaturation" is a double bond (of any type), a triple bond (of any type), or a ring.

A variety of additional terms are defined or otherwise characterized herein.

DETAILED DESCRIPTION

Growth of Group III-V semiconductor nanostructures has been described. For example, Wells, R. L., et al., *Chem. Mater.* 1:4-6 (1989), Guzelian, A. A., et al., *Appl. Phys. Lett.* 69:1432-1434 (1996), Guzelian, A. A., et al., *J. Phys. Chem.* 100:7212-7219 (1996), U.S. Pat. No. 5,505,928, U.S. Pat. No. 6,306,736, U.S. Pat. No. 6,576,291, U.S. Pat. No. 6,821,337, and U.S. Pat. No. 7,138,098 describe the synthesis of substantially spherical Group III-V nanocrystals or quantum dots. And, U.S. Patent Application Publication No. 2003/0214699 describes the use of a metal catalyst to nucleate the growth of rod-shaped Group III-V nanocrystals. The resulting nanocrystals, however, contain non-semiconducting material at one end, which can undesirably affect the electrical properties of the nanocrystals.

Group III Precursors

The Group III atom can be any atom selected from Group III of the periodic table of the elements. In some embodiments, the Group III atom is B, Al, Ga, In, or Tl. In some embodiments, the Group III atom is In.

Preparation of the Diacetate Hydroxide

Commercially available "indium acetate" is typically prepared by converting indium chloride to the hydroxide and reacting with acetic acid as shown in Formula I:

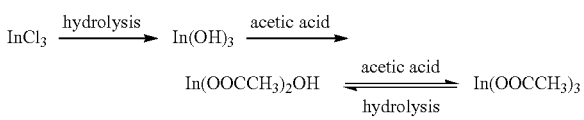

Analysis of various commercially available "indium acetate" samples showed that it was a mixture of $In(OOCCH_3)_{3-n}(OH)_n$, wherein 0<n<1. Use of this mixture in the synthesis of Group III-V nanostructures results in a product that has a wide size distribution.

It was found that the commercially available material could be converted to $In(OOCCH_3)_2OH$ by hydrolysis with water. Initial large scale hydrolysis of the commercial material resulted in a product that showed a 2-band pattern by infrared (IR) spectroscopy; however, after vacuum drying the resultant material overnight at 20° C., a broad band at >2800 cm$^{-1}$ still remained. Further analysis of the resultant material by thermogravimetric analysis (TGA) and inductively coupled plasma atomic emission spectroscopy (ICP-AES) suggested that the resultant material contained a volatile material that was causing the broad band in the >2800 cm$^{-1}$ region. The expected final mass by TGA was found to be 55.5%, whereas a final mass of 53.6% was found after correcting for the baseline. Additionally, a 41.5% indium content was found for the resultant material using ICP-AES compared to the calculated indium content of 45.94%.

Conversely, it was found that vacuum drying the hydrolysis material overnight at 40° C. produced a material that showed a sharp O—H stretch by IR spectroscopy and the absence of a broad band at >2800 cm$^{-1}$. Furthermore, ICP-AES showed an indium content of 45.19% compared to the calculated value of 45.94%.

The present invention provides a process for preparing a Group III diacetate hydroxide of formula (I):

wherein:

$X_1$ is B, Al, Ga, In, or Tl.

In some embodiments, $X_1$ is indium.

The hydrolysis of a Group III acetate mixture is illustrated in Scheme 1.

Scheme 1

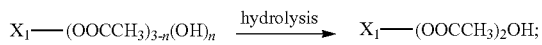

wherein 0<n≤1

In some embodiments, in the formula $X_1$—(OOCCH$_3$)$_{3-n}$(OH)$_n$, 0<n<1.

In the hydrolysis reaction, water and an organic solvent are added to the Group III acetate mixture.

In some embodiments, the organic solvent is selected from the group consisting of methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, diethyl ether dibutyl ether, cyclopentyl methyl ether, anisole, toluene, xylene, heptanes, and mixtures thereof. In some embodiments, the organic solvent is diethyl ether.

In some embodiments, an excess of organic solvent is used in the hydrolysis reaction. In some embodiments, the organic solvent and the Group III acetate mixture are added together in a molar ratio of Group III acetate mixture:organic solvent of from about 1:1 to about 1:500, from about 1:1 to about 1:250, from about 1:1 to about 1:100, from about 1:1 to about 1:50, from about 1:1 to about 1:25, from about 1:1 to about 1:10, from about 1:5 to about 1:500, from about 1:5 to about 1:250, from about 1:5 to about 1:100, from about 1:5 to about 1:50, from about 1:5 to about 1:25, from about 1:5 to about 1:10, from about 1:10 to about 1:500, from about 1:10 to about 1:250, from about 1:10 to about 1:100, from about 1:10 to about 1:50, from about 1:10 to about 1:25, from about 1:25 to about 1:500, from about 1:25 to about 1:250, from about 1:25 to about 1:100, or from about 1:25 to about 1:50. In some embodiments, the Group III acetate mixture and organic solvent are added together in a molar ratio of Group III acetate mixture:organic solvent of from about 1:10 to about 1:100.

In some embodiments an excess of water is used in the hydrolysis reaction. In some embodiments, the Group III acetate mixture and water are added together in a molar ratio of Group III acetate mixture:water of from about 1:1 to about 1:500, from about 1:1 to about 1:250, from about 1:1 to about 1:100, from about 1:1 to about 1:50, from about 1:1 to about 1:25, from about 1:1 to about 1:10, from about 1:5 to about 1:500, from about 1:5 to about 1:250, from about 1:5 to about 1:100, from about 1:5 to about 1:50, from about 1:5 to about 1:25, from about 1:5 to about 1:10, from about 1:10 to about 1:500, from about 1:10 to about 1:250, from about 1:10 to about 1:100, from about 1:10 to about 1:50, from about 1:10 to about 1:25, from about 1:25 to about 1:500, from about 1:25 to about 1:250, from about 1:25 to about 1:100, or from about 1:25 to about 1:50. In some embodiments, the Group III acetate mixture and water are added together in a molar ratio of Group III acetate mixture:water solvent of from about 1:10 to about 1:100.

In some embodiments, the organic solvent is added to the Group III acetate mixture before addition of water. In some embodiments, the organic solvent is added to the Group III acetate mixture at the same time as the addition of water. In some embodiments, water is added to the Group III acetate mixture in an organic solvent by drop-wise addition.

In some embodiments, the hydrolysis reaction is reacted at a temperature of from about 0° C. to about 50° C., from about 0° C. to about 40° C., from about 0° C. to about 30° C., from about 0° C. to about 20° C., from about 5° C. to about 50° C., from about 5° C. to about 40° C., from about 5° C. to about 30° C., from about 5° C. to about 20° C., from about 10° C. to about 50° C., from about 10° C. to about 40° C., from about 10° C. to about 30° C., from about 10° C. to about 20° C., from about 20° C. to about 50° C., from about 20° C. to about 40° C., or from about 20° C. to about 30° C. In some embodiments, the hydrolysis reaction is reacted at a temperature of about 10° C. to about 30° C.

The hydrolysis reaction may proceed for any length of time necessary to achieve conversion of the Group III acetate mixture to the Group III diacetate hydroxide. In some embodiments, the reaction proceeds from about 10 minutes to about 10 hours, from about 10 minutes to about 5 hours, from about 10 minutes to about 3 hours, from about 10 minutes to about 2 hours, from about 10 minutes to about 1 hour, from about 20 minutes to about 10 hours, from about 20 minutes to about 5 hours, from about 20 minutes to about 3 hours, from about 20 minutes to about 2 hours, from about 20 minutes to about 1 hour, from about 30 minutes to about 10 hours, from about 30 minutes to about 5 hours, from about 30 minutes to about 3 hours, from about 30 minutes to about 2 hours, from about 30 minutes to about 1 hour, from about 40 minutes to about 10 hours, from about 40 minutes to about 5 hours, from about 40 minutes to about 3 hours, from about 40 minutes to about 2 hours, from about 40 minutes to about 1 hour, from about 1 hour to about 10 hours, from about 1 hour to about 5 hours, from about 1 hour to about 3 hours, or from about 1 hour to about 2 hours.

In some embodiments, the organic solvent and water are removed from the reaction mixture by distillation at atmospheric pressure or under reduced pressure. In some embodiments, the organic solvent and water are removed from the reaction mixture under reduced pressure at a temperature from about 20° C. to about 100° C., from about 20° C. to about 80° C., from about 20° C. to about 60° C., from about 20° C. to about 40° C., from about 30° C. to about 100° C., from about 20° C. to about 80° C., from about 20° C. to about 60° C., or from about 20° C. to about 40° C. In some embodiments, the organic solvent and water are removed from the reaction mixture under reduced pressure at a temperature from about 20° C. to about 60° C.

In some embodiments, the Group III diacetate hydroxide is dried for a time of between about 10 minutes to about 20 hours, for about 10 minutes to about 15 hours, for about 10 minutes to about 10 hours, for about 10 minutes to about 5 hours, for about 10 minutes to about 3 hours, for about 10 minutes to about 1 hour, for about 20 minutes to about 20 hours, for about 20 minutes to about 15 hours, for about 20 minutes to about 10 hours, for about 20 minutes to about 5 hours, for about 20 minutes to about 3 hours, for about 20 minutes to about 1 hour, for about 30 minutes to about 20 hours, for about 30 minutes to about 15 hours, for about 30 minutes to about 10 hours, for about 30 minutes to about 5 hours, for about 30 minutes to about 3 hours, for about 30 minutes to about 3 hour, for about 40 minutes to about 20 hours, for about 40 minutes to about 15 hours, for about 40 minutes to about 10 hours, for about 40 minutes to about 5 hours, for about 40 minutes to about 3 hours, for about 40 minutes to about 1 hour, for about 1 hour to about 20 hours, for about 1 hour to about 15 hours, for about 1 hour to about 10 hours, for about 1 hour to about 5 hours, or for about 1 hour to about 3 hours.

In some embodiments, the Group III diacetate hydroxide is dried under vacuum.

In some embodiments, the Group III diacetate hydroxide is generated in situ and is used in subsequent reactions without purification.

In some embodiments, the Group III diacetate hydroxide is substantially pure. As used herein, the term "substantially pure" means that the Group III diacetate hydroxide has a purity of greater than or equal to about 90%, greater than or equal to about 92%, greater than or equal to about 95%, greater than or equal to about 97%, greater than or equal to about 98%, or greater than or equal to about 99%.

Preparation of the Group III Precursor

Use of $In(O_2CCH_3)_{3-n}(OH)_n$ in the typical synthesis of InP nanocrystals has several drawbacks. Firstly, since the reagent used is a mixture, the synthetic method will not produce consistent nanocrystal products. This is because a mixture will not allow one in the art to know and control the molar ratio of $In^{3+}$ to long-chain carboxylic acid. Secondly, treatment of $In(O_2CCH_3)_{3-n}(OH)_n$ with long-chain carboxylic acids is expected to form $In(O_2C(CH_2)_mCH_3)_{3-n}(OH)_n$, wherein m is between 7 and 19 and n is between 0 and 1, upon ligand exchange. It is likely that $In(O_2CCH_3)_m(OH)_n$ is not suitable for nanocrystal growth due to the high sensitivity of the reaction kinetics. Thus, if $In(O_2C(CH_2)_mCH_3)_2(OH)$ and $In(O_2C(CH_2)_mCH_3)_3$ react at different rates, the precursor conversion in nanocrystal growth—a step that is critical for obtaining a narrow size distribution—will be more difficult to control than when a single reaction material is used. Therefore, if the value of n is not controlled, then the nanocrystal growth reaction may be irreproducible between batches.

Treatment of $In(O_2CCH_3)_2OH$ with long-chain carboxylic acids produces $In(O_2C(CH_2)_mCH_3)_2OH$ through simple carboxylate ligand exchange, and does not form $In(O_2C(CH_2)_mCH_3)_3$ which is the product of ligand exchange with $In(O_2CCH_3)_3$. Therefore, preparations of InP nanocrystals that use $In(O_2CCH_3)_2OH$ as a starting material proceed through a series of discrete intermediates that are heteroleptic indium hydroxides, whereas preparations that use $In(O_2CCH_3)_3$ as a primary starting material proceed through a series of homoleptic indium carboxylates.

In some embodiments, the present invention provides a method for preparing a Group III precursor of formula III:

  (III)

wherein:
X$_1$ is B, Al, Ga, In, or Tl;
b is between 7 and 19; and
c is 1 or 2.

In some embodiments, the present invention provides a method for preparing a Group III precursor of formula III:

  (III)

wherein:
X$_1$ is B, Al, Ga, In, or Tl;
b is between 7 and 19; and
c is 1 or 2;

the method comprising reacting:
(1) a compound of formula IV:

  (IV)

wherein:
X$_1$ is B, Al, Ga, In, or Tl; and
a is 1 or 2;
(2) with a compound of formula V:

  (V)

wherein:
b is between 7 and 19.

In some embodiments, the present invention provides a process for preparing a Group III precursor of formula VI:

  (II)

wherein:
X$_1$ is B, Al, Ga, In, or Tl; and
d is between 7-19.

In some embodiments, X$_1$ is indium.

The reaction of a Group III diacetate hydroxide with a long-chain carboxylic acid to produce a Group III precursor acid is illustrated in Scheme 2.

Scheme 2

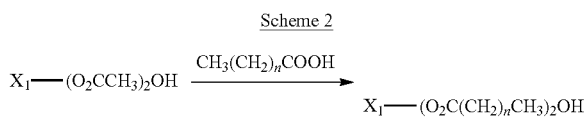

wherein n is between 7-19.

In some embodiments, a long-chain carboxylic acid is reacted with a Group III hydroxide. In some embodiments, the long-chain carboxylic acid is a compound of formula (V):

  (V)

wherein b is 8-18. In some embodiments, b is 10.

The reaction of a Group III hydroxide with a long-chain carboxylic acid is illustrated in Scheme 3.

Scheme 3

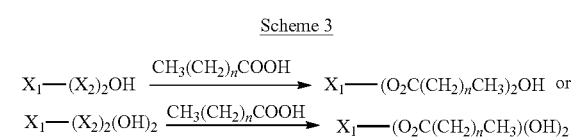

wherein:
X$_1$ is B, Al, Ga, In, or Tl;
X$_2$ is O$_2$CCH$_3$, OH, Cl, or CH$_3$; and
n is between 7-19.

In some embodiments, the Group III precursor is produced in the presence of an organic solvent. In some embodiments, the organic solvent is selected from the group consisting of methyl acetate, ethyl acetate, isopropyl acetate, n-butyl acetate, isobutyl acetate, acetone, methyl ethyl ketone, methyl isobutyl ketone, tetrahydrofuran, 2-methyl-tetrahydrofuran, acetonitrile, methyl t-butyl ether, diethyl ether, dibutyl ether, cyclopentyl methyl ether, anisole, toluene, xylene, heptanes, and mixtures thereof.

In some embodiments, an excess of organic solvent is used in the carboxylate ligand exchange reaction. In some embodiments, the organic solvent and the Group III diacetate hydroxide are added together in a molar ratio of Group III diacetate hydroxide:organic solvent of from about 1:1 to about 1:500, from about 1:1 to about 1:250, from about 1:1 to about 1:100, from about 1:1 to about 1:50, from about 1:1 to about 1:25, from about 1:1 to about 1:10, from about 1:5 to about 1:500, from about 1:5 to about 1:250, from about 1:5 to about 1:100, from about 1:5 to about 1:50, from about 1:5 to about 1:25, from about 1:5 to about 1:10, from about 1:10 to about 1:500, from about 1:10 to about 1:250, from about 1:10 to about 1:100, from about 1:10 to about 1:50, from about 1:10 to about 1:25, from about 1:25 to about 1:500, from about 1:25 to about 1:250, from about 1:25 to about 1:100, or from about 1:25 to about 1:50. In some embodiments, the Group III diacetate hydroxide is added together in a molar ratio of Group III diacetate hydroxide:organic solvent of from about 1:10 to about 1:100.

In some embodiments, a ligand is used in the carboxylic ligand exchange reaction. In some embodiments, the ligand is a fatty acid selected from lauric acid, caproic acid, myristic acid, palmitic acid, stearic acid, and oleic acid. In some embodiments, the ligand is an organic phosphine or an organic phosphine oxide selected from trioctylphosphine oxide (TOPO), trioctylphosphine (TOP), diphenylphosphine (DPP), triphenylphosphine oxide, and tributylphosphine oxide. In some embodiments, the ligand is an amine selected from dodecylamine, oleylamine, hexadecylamine, and octadecylamine. In some embodiments, the ligand is trioctylphosphine oxide (TOPO).

In some embodiments, the carboxylic acid ligand exchange reaction occurs in the presence of a mixture of ligands. In some embodiments, the reaction occurs in the presence of a mixture comprising 2, 3, 4, 5, or 6 different ligands. In some embodiments, the reaction occurs in the presence of a mixture comprising 3 different ligands.

In some embodiments an excess of carboxylic acid is used in the carboxylate ligand exchange reaction. In some embodiments, the compound of formula IV and compound of formula V are added together in a molar ratio of compound of formula IV:compound of formula V of from about 1:1 to about 1:5, from about 1:1 to about 1:3, from about 1:1 to about 1:2.8, from about 1:1 to about 1:2.5, from about 1:1 to about 1:2.2, from about 1:1 to about 1:2.0, from about 1:2.0 to about 1:5, from about 1:2.0 to about 1:3, from about 1:2.0 to about 1:2.8, from about 1:2.0 to about 1:2.5, from about 1:2.2 to about 1:5, from about 1:2.2 to about 1:3, from about 1:2.2 to about 1:2.8, from about 1:2.2 to about 1:2.5, from about 1:2.5 to about 1:5, from about 1:2.5 to about 1:3, from about 1:2.5 to about 1:2.8, from about 1:2.8 to about 1:5, from about 1:2.8 to about 1:3, from about 1:3 to about 1:5, from about 1:3 to about 1:4, from about 1:4 to about 1:5. In some embodiments, the compound of formula IV and compound of formula V are added together in a molar ratio of compound of formula IV:compound of formula V of from about 1:2.0 to about 1:2.8.

In some embodiments an excess of carboxylic acid is used in the carboxylate ligand exchange reaction. In some embodiments, the Group III diacetate hydroxide and carboxylic acid are added together in a molar ratio of Group III diacetate hydroxide:carboxylic acid of from about 1:1 to about 1:5, from about 1:1 to about 1:3, from about 1:1 to about 1:2.8, from about 1:1 to about 1:2.5, from about 1:1 to about 1:2.2, 1:2.2 to about 1:5, from about 1:2.2 to about 1:3, from about 1:2.2 to about 1:2.8, from about 1:2.2 to about 1:2.5, from about 1:2.5 to about 1:5, from about 1:2.5 to about 1:3, from about 1:2.5 to about 1:2.8, from about 1:2.8 to about 1:5, from about 1:2.8 to about 1:3, from about 1:3 to about 1:5, from about 1:3 to about 1:4, from about 1:4 to about 1:5. In some embodiments, the Group III diacetate hydroxide and carboxylic acid are added together in a molar ratio of Group III diacetate hydroxide:carboxylic acid of from about 1:2.2 to about 1:2.8.

In some embodiments, the carboxylate ligand exchange reaction occurs at a first temperature of from about 20° C. to about 100° C., from about 20° C. to about 80° C., from about 20° C. to about 60° C., from about 20° C. to about 50° C., from about 40° C. to about 100° C., from about 40° C. to about 80° C., from about 40° C. to about 60° C., from about 40° C. to about 50° C., from about 50° C. to about 100° C., from about 50° C. to about 80° C., from about 50° C. to about 60° C., from about 60° C. to about 100° C., from about 60° C. to about 80° C., or from about 80° C. to about 100° C. In some embodiments, the carboxylate exchange reaction occurs at a first temperature of about 20° C. to about 60° C.

The first temperature of the carboxylate ligand exchange reaction may proceed for any length of time necessary to melt the solid materials of the Group III diacetate mixture. In some embodiments, the first temperature of the carboxylate ligand exchange reaction proceeds from about 10 minutes to about 10 hours, from about 10 minutes to about 5 hours, from about 10 minutes to about 3 hours, from about 10 minutes to about 2 hours, from about 10 minutes to about 1 hour, from about 20 minutes to about 10 hours, from about 20 minutes to about 5 hours, from about 20 minutes to about 3 hours, from about 20 minutes to about 2 hours, from about 20 minutes to about 1 hour, from about 30 minutes to about 10 hours, from about 30 minutes to about 5 hours, from about 30 minutes to about 3 hours, from about 30 minutes to about 2 hours, from about 30 minutes to about 1 hour, from about 40 minutes to about 10 hours, from about 10 minutes to about 5 hours, from about 10 minutes to about 3 hours, from about 10 minutes to about 2 hours, from about 10 minutes to about 1 hour, from about 40 minutes to about 10 hours, from about 40 minutes to about 5 hours, from about 40 minutes to about 3 hours, from about 40 minutes to about 2 hours, from about 40 minutes to about 1 hour, from about 1 hour to about 10 hours, from about 1 hour to about 5 hours, from about 1 hour to about 3 hours, or from about 1 hour to about 2 hours.

In some embodiments, the carboxylate ligand exchange reaction occurs at a second temperature of from about 60° C. to about 200° C., from about 60° C. to about 180° C., from about 60° C. to about 150° C., from about 60° C. to about 100° C., from about 100° C. to about 200° C., from about 100° C. to about 180° C., from about 100° C. to about 150° C., from about 150° C. to about 200° C., from about 150° C. to about 180° C., or from about 180° C. to about 200° C. In some embodiments, the carboxylate exchange reaction occurs at a second temperature of about 100° C. to about 200° C.

The second temperature of the carboxylate ligand exchange reaction may proceed for any length of time necessary effect the carboxylate ligand exchange. In some embodiments, the second temperature of the carboxylate ligand exchange reaction proceeds from about 10 minutes to about 10 hours, from about 10 minutes to about 5 hours, from about 10 minutes to about 3 hours, from about 10 minutes to about 2 hours, from about 10 minutes to about 1 hour, from about 20 minutes to about 10 hours, from about 20 minutes to about 5 hours, from about 20 minutes to about 3 hours, from about 20 minutes to about 2 hours, from about 20 minutes to about 1 hour, from about 30 minutes to about 10 hours, from about 30 minutes to about 5 hours, from about 30 minutes to about 3 hours, from about 30 minutes to about 2 hours, from about 30 minutes to about 1 hour, from about 40 minutes to about 10 hours, from about 10 minutes to about 5 hours, from about 10 minutes to about 3 hours, from about 10 minutes to about 2 hours, from about 10 minutes to about 1 hour, from about 40 minutes to about 10 hours, from about 40 minutes to about 5 hours, from about 40 minutes to about 3 hours, from about 40 minutes to about 2 hours, from about 40 minutes to about 1 hour, from about 1 hour to about 10 hours, from about 1 hour to about 5 hours, from about 1 hour to about 3 hours, or from about 1 hour to about 2 hours.

In some embodiments, excess carboxylic acid is removed from the reaction mixture by distillation at atmospheric pressure or under reduced pressure. In some embodiments, the excess carboxylic acid is removed from the reaction mixture under reduced pressure at a temperature from about 60° C. to about 200° C., from about 60° C. to about 180° C., from about 60° C. to about 150° C., from about 60° C. to about 100° C., from about 100° C. to about 200° C., from about 100° C. to about 180° C., from about 100° C. to about 150° C., from about 150° C. to about 200° C., from about 150° C. to about 180° C., or from about 180° C. to about 200° C. In some embodiments, the organic solvent and water are removed from the reaction mixture under reduced pressure at a temperature from about 100° C. to about 200° C.

In some embodiments, the Group III precursor is generated in situ and is used in subsequent reactions without purification.

Group V Precursors

The Group V atom can be any atom selected from Group V of the periodic table of the elements. In some embodiments, the Group V atom is N, P, As, Sb, or Bi.

In some embodiments, the Group V precursor comprises a trisubstituted Group V atom. In some embodiments, the trisubstituted Group V atom is (a) a trialkyl substituted Group V atom comprising an unbranched and unsubstituted alkyl group, (b) an H₃ substituted Group V atom, (c) an alkyl substituted Group V atom comprising an unbranched and unsubstituted alkyl group, (d) a dialkyl substituted Group V atom comprising an unbranched and unsubstituted alkyl group, or (e) a tris(trialkylsilyl) substituted Group V atom. In some embodiments, the Group V precursors of the invention is a trialkyl substituted, an alkyl substituted, or dialkyl substituted Group V atom. In some embodiments, the Group V precursor is tris(trimethylsilyl)phosphine.

Where the Group V precursor is a trisubstituted Group V atom, the three substituents on the atom in the Group V precursor can be identical or distinct. The three substituents can be independently any organic group or hydrogen, for example. In some embodiments, the Group V precursor is a Group V organometallic compound, e.g., which can be used in a low temperature route or in a high temperature precursor decomposition route to solution-based synthesis of Group III-V semiconductor nanostructures.

In some embodiments, the Group V precursor comprises a Group V atom substituted with three unsaturated groups (e.g., any group including at least one double or triple bond or ring, including, but not limited to, alkenyl, alkynyl, acyl, and aryl groups). For example, the Group V precursor can be triallylphosphine, trivinylphosphine, tributadienylphosphine, trialkylethynylphosphine, trialkylethenylphosphine, tri(4-phenylethynyl)phosphine, or trialkylphenylethynylphosphine. See, e.g., Beletskaya et al., *Organic Letters* 5:4309-4311 (2003) for a description of ethynylphosphine synthesis and example ethynylphosphines. As another example, the Group V precursor can include a Group V atom substituted with three furyl or furfuryl groups; e.g., the Group V precursor can be tri-2-furylphosphine or tri-2-furfurylphosphine. See, e.g., Farina and Krishnan, *J. Am. Chem. Soc.* 113:9585-9595 (1991).

In some embodiments, the Group V precursor comprises a triacyl substituted Group V atom. The acyl group can be unsubstituted or substituted. For example, the Group V precursor can be a triacylphosphine or a triacylarsine, e.g., tribenzoylphosphine, trialkylbenzoylphosphine, trihexylbenzoylphosphine, trialkoylphosphine, or trihexoylphosphine. Synthesis of acyl phosphines has been described, e.g., in Tyka, et al., *Roczniki. Chem.* 35:183 (1961), Tyka, et al., *Ref Zh. Khim.* 1 Zh 245 (1962), Barycki, et al., *Tetrahedron Letters* 10:857 (1978), and Kost, *Tetrahedron Letters* 22:1983 (1979).

In some embodiments, the Group V precursor comprises a triaryl substituted Group V atom. The aryl group can be unsubstituted or substituted. The substituent optionally comprises an electron donating group or an electron withdrawing group (a wide variety of electron donating and withdrawing groups are known in the art and can be adapted for use in the present invention). In one class of example embodiments, the Group V precursor comprises a tribenzyl substituted Group V atom; for example, the Group V precursor can be tribenzylphosphine or tribenzylarsine.

In some embodiments, the Group V precursor comprises a Group V atom substituted with three carboxamide groups. Thus, for example, the Group V precursor can be a tricarboxamide phosphine, e.g., N,N,N,N,N,N-hexaethylphosphine tricarboxamide.

In some embodiments, the Group V precursor comprises a trialkyl substituted Group V atom comprising a substituted and/or branched alkyl group. For example, the Group V precursor can include a tri-t-butyl substituted Group V atom; e.g., the Group V precursor can be tri-t-butylphosphine.

International Patent Appl. Publication No. WO 03/054953 suggests the use of precursors including a tri-alkyl substituted Group V atom; however, only n-alkyl substituents are described. Precursors with branched and/or substituted alkyl substituents on the Group V atom can unexpectedly work considerably better in nanostructure synthesis reactions, since they can react more quickly and/or form more stable by-products than do tri-n-alkyl substituted Group V atoms (e.g., tri-n-alkyl phosphines or arsines). Similarly, precursors with aryl substituents on the Group V atom (e.g., tribenzylphosphine) can also react more quickly and/or form more stable by-products than do tri-n-alkyl substituted Group V atoms (e.g., tri-n-alkyl phosphines).

In some embodiments, the Group V precursor is a Group V inorganic compound. For example, in some embodiments, the Group V precursor comprises a Group V atom substituted with three carboxylate moieties or with three phosphinate moieties. In some embodiments, the Group V atom is P such that the Group V precursor is a phosphite ester.

In general, without intending to be limited by any particular mechanism, unsaturated substituents on the P or other Group V element can result in cycloadditions, thus changing the bonding character between the Group III and Group V atoms. Group V precursors that contain unsaturated moieties bonded to the Group V atom can promote pi-backbonding from the late metal indium or other Group III atom to the Group V atom, thus strengthening the III-V interaction and weakening bonds to the moieties attached to the Group III and V atoms. This can result in enhanced cleavage of organometallic bonds to the indium or other Group III metal center.

Production of Group III-V Nanostructures

The present invention provides a method for production of Group III-V semiconductor nanostructures. In the methods, a Group III precursor and a Group V precursor are provided, and the Group III and Group V precursors are reacted to produce the nanostructures.

In some embodiments, the Group III and Group V precursors are reacted in the presence of at least one surfactant. In some embodiments, the precursors can be reacted in the presence of a first surfactant, a second surfactant, or a mixture of first and second surfactants. In some embodiments, the first surfactant is selected from the group consisting of tri-n-alkyl phosphines (e.g., TOP and tri-n-butyl phosphine (TBP), and $C_{12}$-$C_{30}$ tri-n-alkyl phosphines, e.g., tri-n-dodecyl phosphine or tri-n-hexadecyl phosphine), tri-n-alkyl phosphine oxides (e.g., TOPO), alkyl amines (e.g., monoalkyl amines and bialkyl amines, or trialkyl amines such as trioctylamine), alkyl-thiols, and aryl-thiols. Suitable first surfactants also include unsaturated Group V derivatives; the first surfactant can comprise a Group V atom substituted with three unsaturated groups (e.g., alkenyl or alkynyl groups). Examples include trisalkylphenylethynyl-phosphines, e.g., tri(ethynylbenzene-hexyl)phosphine, tris(ethynylbenzene-pentyl)phosphine, and other unsaturated phosphines.

Suitable second surfactants include, but are not limited to, alkyl amines (e.g., mono-, bi-, and tri-alkyl amines) and phosphonic acids (e.g., a $C_{2-30}$ alkylphosphonic acid), phosphinic acids (e.g., a $C_{2-30}$ bialkylphosphinic acid), carboxylic acids (e.g., a $C_{2-30}$ alkylcarboxylic acid), boronic acids, and sulfonic acids, as well as deprotonated forms or condensates thereof.

In some embodiments, the Group III and Group V precursors are reacted in the presence of a non-coordinating solvent, e.g., an alkane or an alkene, e.g., hexadecane, octadecane, octadecene, phenyldodecane, phenyltetradecane, or phenylhexadecane. In some embodiments, the non-coordinating solvent has a boiling point greater than 100° C. The composition optionally also includes a first and/or second surfactant, e.g., such as those described herein, e.g., a carboxylic acid second surfactant. Alternatively or in addition, the composition optionally includes a sacrificial oxide acceptor, e.g., a pi-acid such as triphenylphosphine. In some embodiments, the Group III and Group V precursors are reacted in the presence of the non-coordinating solvent and a first and/or second surfactant (e.g., any of those described herein). For example, the Group III and Group V precursors can be reacted in the presence of the non-coordinating solvent (e.g., phenylhexadecane) and a carboxylic acid (e.g., stearic acid), and optionally also in the presence of a sacrificial oxide acceptor (e.g., triphenylphosphine).

Using a mixture of surfactants, varying the ratio of the surfactant(s) to the precursors, and/or varying the ratio of the precursors to each other permits the shape and/or size of the resulting nanostructures to be controlled. Thus, in one class of embodiments, reacting the Group III and Group V precursors comprises reacting the Group III and Group V precursors in the presence of at least a first surfactant and a second surfactant, whereby the shape of the nanostructures produced is capable of being controlled by adjusting the ratio of the first and second surfactants. For example, the molar ratio of the first and second surfactants can be adjusted to produce substantially spherical nanocrystals, nanorods, branched nanostructures, and/or nanotetrapods. Additional surfactants can also be used to help control the shape of the resulting nanocrystals. Thus, in some embodiments, the Group III and Group V precursors are reacted in the presence of a first surfactant, a second surfactant, and a third surfactant.

In a related class of embodiments, reacting the Group III and Group V precursors comprises reacting the Group III and Group V precursors in the presence of a second surfactant, whereby the shape of the nanostructures produced is capable of being controlled by adjusting the ratio of the second surfactant and the Group III or Group V precursor. For example, the ratio of the second surfactant and the Group III or Group V precursor can be adjusted to produce substantially spherical nanocrystals, nanorods, branched nanostructures, and/or nanotetrapods.

In another related class of embodiments, the ratio of the Group III and Group V precursors is adjusted to control the shape of the nanostructures produced. As for the embodiments above, the molar ratio of the Group III and Group V precursors can be adjusted to produce, e.g., substantially spherical nanocrystals, nanorods, branched nanostructures, and/or nanotetrapods.

In some embodiments, the Group III precursor to Group V precursor are added together in a molar ratio of Group III precursor:Group V precursor of between about 0.5:1 to about 2:1, between about 0.5:1 to about 1.8:1, between about 0.5:1 to about 1.6:1, between about 0.5:1 to about 1.4:1, between about 0.5:1 to about 1.2:1, between about 0.5:1 to about 1:1, 1:1 to about 2:1, between about 1:1 to about 1.8:1, between about 1:1 to about to about 1.6:1, between about 1:1 to about 1.4:1, between about 1:1 to about 1.2:1, between about 1:1 to about 1.1:1, between about 1.1:1 to about 2:1, between about 1.1:1 to about 1.8:1, between about 1.1:1 to about 1.6:1, between about 1.1 to about 1.4:1, or between about 1.1 to about 1.2:1.

Alternatively or in addition, the temperature can be controlled to control the shape and/or size distribution of the resulting nanostructures. Thus, in one class of embodiments, reacting the Group III and Group V precursors to produce the nanostructures includes heating at least one surfactant (e.g., a first and a second surfactant) to a first temperature; contacting the Group III and Group V precursors and the heated surfactant, whereby the Group III and Group V precursors react to form nuclei capable of nucleating nanostructure growth; and maintaining the Group III and Group V precursors, the surfactant, and the nuclei at a second temperature. The second temperature permits growth of the nuclei to produce the nanostructures, whereby the Group III and Group V precursors react to grow the nanostructures from the nuclei. The first (nucleation) temperature is typically greater than the second temperature, e.g., by about 40-80° C., about 20-40° C., about 10-20° C., about 5-10° C., or about 0-5° C.; the first and second temperatures can, however, be equal, or the first temperature can be less than the second temperature (e.g., by about 40-80° C., about 20-40° C., about 10-20° C., about 5-10° C., or about 0-5° C.). In some embodiments, the first temperature is between about 250° C. and about 450° C., between about 250° C. and about 420° C., between about 250° C. and about 400° C., between about 250° C. and about 350° C., between about 250° C. and about 300° C., between about 300° C. and about 450° C., between about 300° C. and about 420° C., between about 300° C. and about 400° C., between about 300° C. and about 350° C., between about 350° C. and about 450° C., between about 350° C. and about 420° C., between about 350° C. and about 400° C., between about 400° C. and about 450° C., between about 400° C. and about 420° C., or between about 420° C. and about 450° C.

Yield of nanostructures from the reaction is optionally increased by removal of one or more by-products during the reaction. Thus, in some embodiments, the Group III and Group V precursors react to produce the nanostructures and a by-product that has a boiling point or sublimation temperature that is less than the second temperature. The methods include removing at least a portion of the by-product as a vapor.

The Group III and Group V precursors can be added either simultaneously or sequentially to a reaction vessel in which nanostructure synthesis is performed. Thus, in one class of embodiments, reacting the Group III and Group V precursors to produce the nanostructures includes contacting the Group III and Group V precursors, which form a Group III-V complex. The Group III-V complex is then reacted to produce the nanostructures. The complex is optionally isolated after it is formed.

The nanostructures produced by the methods can be essentially any shape and/or size. For example, the resulting nanostructures can include nanocrystals, substantially spherical nanocrystals, nanorods, branched nanostructures, and/or nanotetrapods. Similarly, the nanostructures can comprise essentially any Group III-V semiconductor, including, but not limited to, InN, InP, InAs, InSb, GaN, GaP, GaAs, GaSb, AlN, AlP, AlAs, or AlSb.

Another general class of embodiments provides high temperature methods for production of Group III-V semiconductor nanostructures. In the methods, a Group III precursor and a Group V precursor are provided. The Group III and Group V precursors are reacted at a first temperature of at least 200° C. to produce the nanostructures. In some embodiments, the first temperature is between about 200° C. and about 400° C., between about 200° C. and about 350° C., between about 200° C. and about 300° C., between about 200° C. and about 250° C., between about 250° C. and about 400° C., between about 250° C. and about 350° C., between about 250° C. and about 300° C., between about 300° C. and about 400° C., between about 300° C. and about 350° C., or between about 350° C. and about 400° C.

In some embodiments, the composition of Group III and Group V precursors is maintained at a preselected temperature, for example, to facilitate nanostructure nucleation, growth, annealing, or the like. Thus, in one class of embodiments, the precursors are maintained at a temperature between between about 200° C. and about 400° C., between about 200° C. and about 350° C., between about 200° C. and about 300° C., between about 200° C. and about 250° C., between about 250° C. and about 400° C., between about 250° C. and about 350° C., between about 250° C. and about 300° C., between about 300° C. and about 400° C., between about 300° C. and about 350° C., or between about 350° C. and about 400° C.

The precursors can be added either simultaneously or sequentially to a reaction vessel in which nanostructure synthesis is performed. Thus, in one class of embodiments, reacting the Group III and Group V precursors to produce the nanostructures includes contacting the Group III and Group V precursors, which form a Group III-V complex. The Group III-V complex is then reacted to produce the nanostructures. The complex is optionally isolated after it is formed.

Co-Products

Reacting precursors to produce nanostructures typically produces both the desired nanostructures and at least one co-product. Selecting precursors such that the co-product is relatively stable can be advantageous (e.g., can assist in preventing undesirable side reactions). In one aspect, the invention provides methods of synthesizing nanostructures that result in production of the nanostructures and a relatively stable co-product.

Thus, one general class of embodiments provides methods for production of Group III-V semiconductor nanostructures. In the methods, a Group V precursor comprising a Group V atom and a Group III precursor comprising a Group III atom are provided and reacted to produce the nanostructures and at least one co-product. In one class of embodiments, the co-product is an ester, a ketone, or an ether.

Reaction of a variety of combinations of Group III and Group V precursors results in formation of an ether, ketone, or ester. For example, when the Group V precursor comprises a trialkyl substituted Group V atom and the Group III precursor comprises a tricarboxylate substituted Group III atom, the co-product can be an ester. As another example, the Group V precursor can comprise a triacyl substituted Group V atom, the Group III precursor a Group III atom substituted with three cyclic ketone groups (e.g., tris-alpha-cyclohexanone indium (III)), and the co-product an ester. As yet another example, the Group V precursor can comprise a triacyl substituted Group V atom, the Group III precursor a Group III alkoxy or aryloxy, and the co-product an ester. As yet another example, the Group V precursor can comprise a triacyl substituted Group V atom, the Group III precursor a tris-Cp or tris-(substituted Cp) Group III atom (e.g., an indium tris-Cp or tris-(substituted Cp) compound, e.g., tris-cyclopentadienyl indium(III) or tris(n-hexyl cyclopentadienyl) indium(III)), and the co-product a ketone. As yet another example, the Group V precursor can comprise triphenylphosphine or a tri-alkylphosphine, the Group III precursor tri-alkoxyindium, and the co-product an ether.

The methods optionally include substantially purifying the nanostructures away from the co-product (e.g., prior to their use or incorporation into an optoelectronic device, a nanocomposite, or the like). For example, an ester, ketone, or ether co-product can be evaporated using a vacuum and/or heat.

Essentially all of the features noted above apply to this embodiment as well, as relevant; e.g., for types and composition of nanostructures produced, Group III and Group V precursors, and/or the like.

Nanostructures (e.g., nanocrystals, substantially spherical nanocrystals, nanorods, branched nanostructures, or nanotetrapods) produced by the methods form another feature of the invention.

Another general class of embodiments provides compositions related to the methods. The composition comprises a Group V precursor comprising a Group V atom, a Group III precursor comprising a Group III atom, a nanostructure comprising the Group III atom and the Group V atom, and a co-product. In one class of embodiments, the co-product is an ester, a ketone, or an ether. The nanostructure and the co-product were produced by reaction of the precursors.

Essentially all of the features noted above apply to this embodiment as well, as relevant; e.g., for types and composition of nanostructures produced, Group III and Group V precursors, co-products, and/or the like.

By-Product Removal

In one aspect, the invention provides methods for production of nanostructures that can, e.g., increase yield of nanostructures from nanostructure synthesis reactions through removal of a by-product by passing the reaction mixture into the gas phase. In the methods, one or more precursors are provided and reacted at a reaction temperature (e.g., a nanostructure growth temperature) to produce the nanostructures and at least one by-product. The by-product has a boiling point or sublimation temperature that is less than the reaction temperature. At least a portion of the by-product is removed in the gas phase. Removal of the by-product pushes the reaction equilibrium toward making more nanostructures.

The nanostructures can be of essentially any type and/or composition. For example, the nanostructures can be semiconductor nanostructures, e.g., Group Group III-V semiconductor nanostructures.

In one class of embodiments, the one or more precursors include a Group V precursor comprising a Group V atom and a Group III precursor comprising a Group III atom. The resulting nanostructures can comprise essentially any Group III-V semiconductor, including, but not limited to, InN, InP, InAs, InSb, GaN, GaP, GaAs, GaSb, AlN, AlP, AlAs, and AlSb. A number of Group III and Group V precursors and reaction temperatures can be selected such that the by-product formed has a boiling point or sublimation temperature less than the reaction temperature.

Surfactants

As noted above, one or more surfactants are typically used in a nanostructure synthesis reaction, to assist in controlling shape and/or size of the resulting nanostructures, to maintain solubility and prevent aggregation of the nanostructures, and/or the like. A number of suitable surfactants are described herein and known in the art and can be used singly or in various combinations. Examples include, but are not limited to, tri-n-alkyl phosphines (e.g., TOP and tri-n-butyl phosphine (TBP)), tri-n-alkyl phosphine oxides (e.g., TOPO), alkyl amines (e.g., monoalkyl amines and bialkyl amines, or trialkyl amines such as trioctylamine), alkyl-thiols, aryl-thiols, unsaturated Group V derivatives (e.g., trisalkylphenylethynylphosphines, e.g., tri(ethynylbenzene-hexyl)phosphine and tris(ethynylbenzene-pentyl)phosphine), phosphonic acids (e.g., a $C_{2-30}$ alkylphosphonic acid), phosphinic acids (e.g., a $C_{2-30}$ bialkylphosphinic acid), carboxylic acids (e.g., a $C_{2-30}$ alkylcarboxylic acid), boronic acids, and sulfonic acids. As noted, in certain embodiments, the same substance can serve as both a precursor and a surfactant.

A suitable surfactant (or combination of surfactants) for use with a given set of precursors can be determined by experimentation as is known in the art. Factors affecting choice of surfactant(s) can include, for example, reaction temperature, choice of precursors, and desired size and shape of the nanostructures to be produced. For example, if the nanostructures are to be nucleated and/or grown at high temperature, the surfactant(s) must be stable at that temperature. As another example, the relative nucleophilicity of the precursor(s) and surfactant(s) can affect the choice of surfactant; for example, tri-n-alkyl phosphines are typically not used as surfactants in combination with unsaturated phosphine Group III precursors. As a specific example, for reaction of a $Cp_3In$ Group III precursor with a tribenzoyl-phosphine Group V precursor to form InP nanostructures, tri-n-alkyl phosphine surfactants can knock the tribenzoyl-phosphine off of the $Cp_3In$ coordination site, favoring the formation of Indium metal instead of InP, and are thus less desirable for use as surfactants with these precursors. As another example, if the surfactant is capable of reacting with the Group V precursor, it is typically used in combination with a Group III precursor that reacts at a lower temperature. As just one specific example, a trialkoyl phosphine can be used as the Group III precursor and tri(ethynylbenzene-hexyl)phosphine as the first surfactant, since the trialkoyl phosphine will react at a lower temperature than the tri(ethynylbenzene-hexyl)phosphine will.

Methods and compositions including surfactants of the invention (e.g., tri-unsaturated Group V derivatives) form a feature of the invention. Thus, one general class of embodiments provides methods for production of nanostructures. In the methods, a surfactant comprising a Group V atom substituted with three unsaturated groups and one or more precursors are provided. The one or more precursors are reacted in the presence of the surfactant to produce the nanostructures. In one class of embodiments, the nanostructures are Group III-V semiconductor nanostructures; in this class of embodiments, the one or more precursors can, e.g., include a Group V precursor comprising a Group V atom and a Group III precursor comprising a Group III atom.

The three unsaturated groups on the Group V atom in the surfactant optionally comprise alkenyl or alkynyl groups. Thus, for example, the surfactant can be a trisalkylphenyl-ethynylphosphine, e.g., trisalkylphenylethynylphosphine or tri(ethynylbenzene-hexyl)phosphine.

Compositions related to the methods are also a feature of the invention. One general class of embodiments provides a composition including a surfactant comprising a Group V atom substituted with three unsaturated groups and one or more precursors. The composition optionally also includes one or more nanostructures, e.g., Group III-V semiconductor nanostructures. The one or more precursors can, e.g., include a Group V precursor comprising a Group V atom and a Group III precursor comprising a Group III atom.

As for the embodiments above, the three unsaturated groups on the Group V atom in the surfactant optionally comprise alkenyl or alkynyl groups. Thus, for example, the surfactant can be a trisalkylphenylethynylphosphine, e.g., trisalkylphenylethynylphosphine or tri(ethynylbenzene-hexyl)phosphine.

Nanostructures

As noted, nanostructures (including, but not limited to, nanocrystals, substantially spherical nanocrystals, nanorods, branched nanostructures, or nanotetrapods) produced by any of the methods herein form another feature of the invention, as do devices, e.g., photovoltaic devices, including such nanostructures. Since the methods do not require the use of a non-semiconducting metal catalyst to initiate nanostructure growth, the resulting nanostructures are typically free of non-semiconducting (e.g., metallic) regions. Such absence of metallic regions in the nanostructures is desirable in many applications, e.g., when the nanostructures are to avoid charge recombination.

Thus, one general class of embodiments provides a nanostructure comprising a Group III-V semiconductor. The nanostructure is substantially free of metallic noble, Group Ib, Group IIb, Group IIIb, and transition metal elements (e.g., such metallic elements are undetectable by a technique such as XRD). The nanostructure is optionally substantially free of any metallic metal element (e.g., free of metallic indium as compared to semiconducting indium phosphide).

In one class of embodiments, the nanostructure is a branched nanostructure or a nanostructure having an aspect ratio greater than about 1.2, and the nanostructure has a wurtzite crystal structure or a zinc blende-wurtzite mixed crystal structure. For example, in one class of embodiments, the nanostructure is a nanotetrapod; nanotetrapods typically have a zinc blende-wurtzite mixed crystal structure, with a zinc blende crystal structure in their central region and a wurtzite crystal structure in their arms. In another class of embodiments, the nanostructure is a nanorod having an aspect ratio greater than about 1.2, greater than about 1.5, greater than about 2, greater than about 3, or greater than about 5. Nanorods typically have a wurtzite crystal structure.

Use of the novel precursors and/or surfactants of the invention can also produce nanostructures (of any size and/or shape, including, e.g., tetrahedral and substantially spherical nanocrystals as well as nanorods and branched nanostructures) that are substantially free of Si (since Si-containing precursors need not be used), substantially free of phosphonic acid, phosphinic acid, and/or carboxylic acid, and/or substantially free of tri-n-alkyl phosphines (e.g., TOP) and tri-n-alkyl phosphine oxides (e.g., TOPO) (since other surfactants can be used). Use of certain precursors described herein can, e.g., result in nanostructures having a sulfonic acid, or a boronic acid, or a deprotonated form or a condensate thereof, associated with a surface of the nanostructures. Similarly, use of certain precursors and/or surfactants described herein can, e.g., result in nanostructures having a carboxylic acid or a deprotonated form or a condensate thereof, and/or a surfactant comprising a Group V atom substituted with three unsaturated groups, associated with a surface of the nanostructures.

Use of the methods and compositions of the invention can, e.g., decrease or prevent premature termination of nanostructure growth, resulting in larger nanostructures than were previously obtainable. Thus, for example, one general class of embodiments provides a nanostructure comprising a Group III-V semiconductor, the nanostructure being a tetrahedral nanostructure. In one class of embodiments, the nanostructure has an edge at least 10 nm in length (e.g., at least 12 nm, at least 15 nm, or at least 20 nm). All six edges are optionally at least 10 nm in length. The nanostructure can be, e.g., a nanocrystal, and can have a zinc blende crystal structure.

Essentially all of the features noted above apply to this embodiment as well, as relevant; e.g., for composition of the nanostructure. For example, the Group III-V semiconductor can include a first atom selected from the group consisting of N, P, As, Sb, and Bi and a second atom selected from the group consisting of B, Al, Ga, In, and Tl (e.g., InP and InAs). As for the embodiments described above, the nanostructure is optionally substantially free of metallic elements and n-alkyl phosphine oxides. Similarly, the nanostructure can have a carboxylic acid or a deprotonated form or a condensate thereof, and/or a surfactant comprising a Group V atom substituted with three unsaturated groups, associated with a surface of the nanostructure. The invention also includes a population of such nanostructures.

A device including a plurality of such nanostructures is also a feature of the invention, for example, a photovoltaic or other opto-electronic device. Packing of the tetrahedral nanostructures in such a device can, e.g., provide a favorable path for movement of electrons and/or holes through adjacent nanostructures disposed between opposing electrodes. Photovoltaic devices incorporating nanostructures are described, e.g., in U.S. Patent Application Publication No. 2015/0126628.

Compositions including nanostructures and one or more Group III precursor, Group V precursor, and/or surfactant of the invention are also a feature of the invention. Thus, one general class of embodiments provides a composition that includes one or more nanostructures (e.g., Group III-V semiconductor nanostructures) having a surfactant associated (covalently or non-covalently) with a surface thereof. The surfactant comprises a Group V atom substituted with three unsaturated groups, e.g., alkenyl or alkynyl groups. Essentially all of the features noted above apply to this embodiment as well, as relevant; e.g., for types and composition of nanostructures, types of surfactant, and the like. For example, the surfactant can be a trisalkylphenylethynylphosphine, e.g., trisalkylphenylethynylphosphine or tri(ethynylbenzene-hexyl)phosphine.

Another general class of embodiments provides a composition that includes one or more Group III-V semiconductor nanostructures and a Group V precursor of the invention. For example, the Group V precursor can comprise a Group V atom substituted with three unsaturated groups, a triacyl substituted Group V atom, a Group V atom substituted with three carboxamide groups, a triaryl substituted Group V atom, or a Group V atom substituted with three carboxylate moieties or with three phosphinate moieties, for example, any such precursors described herein. For example, the Group V precursor can be triallylphosphine, trivinylphosphine, tributadienylphosphine, trialkylethynylphosphine, trialkylethenylphosphine, tri(4-phenylethynyl)phosphine, trialkylphenylethynylphosphine, a triacylphosphine, tribenzoylphosphine, trialkylbenzoylphosphine, trihexylbenzoylphosphine, trialkoylphosphine, trihexoylphosphine, a tricarboxamide phosphine, N,N,N,N,N,N-hexaethylphosphine tricarboxamide, tribenzylphosphine, or tribenzylarsine. As another example, the Group V precursor can include a Group V atom substituted with three furyl or furfuryl groups; e.g., the Group V precursor can be tri-2-furylphosphine or tri-2-furfurylphosphine. As yet another example, the Group V precursor can be a phosphite ester. The composition optionally includes a Group III precursor, a first surfactant, a second surfactant, and/or a non-coordinating solvent. Essentially all of the features noted above apply to this embodiment as well, as relevant; e.g., for types and composition of nanostructures, Group III precursors, first and second surfactants, solvents, sacrificial oxide acceptors, and the like.

Yet another general class of embodiments provides a composition that includes one or more Group III-V semiconductor nanostructures and a Group III precursor of the invention. For example, the Group III precursor can comprise a Group III atom which is directly bonded to at least one oxygen atom; one or more phosphonate, phosphinate, and/or carboxylate moieties other than an acetate moiety bonded to a Group III atom; a Group III metal oxide; a Group III alkoxy or aryloxy; or a Group III atom substituted with three unsaturated groups. Thus, the Group III precursor can be, e.g., indium phosphonate, indium carboxylate, indium tristearate, indium oxide, gallium oxide, indium phenoxy, triallyl indium, trivinyl indium, tributadiene indium, trialkylethynyl indium, trialkylethenyl indium, tri-4-phenylethynyl indium, trialkylphenylethynyl indium, tris-alpha-cyclohexanone indium (III), an indium tris-Cp compound, an indium tris-(substituted Cp) compound, tris-cyclopentadienyl indium(III) or tris(n-hexyl cyclopentadienyl) indium(III). The composition optionally includes a Group V precursor, a first surfactant, a second surfactant, and/or a non-coordinating solvent. Essentially all of the features noted above apply to this embodiment as well, as relevant; e.g., for types and composition of nanostructures, Group V precursors, first and second surfactants, solvents, sacrificial oxide acceptors, and the like.

EXAMPLES

The following sets forth a series of experiments that demonstrate the synthesis of a Group III precursor and use of the precursor to generate Group III-Group V nanostructures. It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: Control Reaction for Preparation of $In(O_2CCH_3)_2OH$

In the glovebox, three 500 mg samples (each from a different lot) of indium acetate (Indium Corporation, Utica, N.Y.) were weighed. To each sample was added 10 mL of anhydrous diethyl ether. The sample was vigorously shaken. Outside the glovebox, the samples were filtered through a M-porosity filtration/fritted funnel to collect the solids. In order to rinse the vials, hexanes were added and the slurry that formed was filtered. The solids were dried under dynamic vacuum for between 5 to 10 minutes. Each solid was analyzed by Fourier transform infrared spectroscopy (FTIR).

In the glovebox, three 500 mg samples of indium acetate (Indium Corporation, Utica, N.Y.) were weighed. To each sample was added 10 mL of anhydrous diethyl ether and 1 mL of deionized water. The samples were vigorously shaken. Outside the glovebox, the samples were filtered through a M-porosity filtration/fritted funnel to collect the solids. In order to rinse the vials, hexanes were added and the slurry that formed was filtered. The solid samples were dried under dynamic vacuum. After 10 minutes, the material was not completely dried. Each solid sample was analyzed by FTIR after 10 minutes of drying time and after 12 hours of drying time.

The three samples treated with diethyl ether—no deionized water—provided equivalent FTIR spectra featuring a 5-band pattern in the region from 1200-1800 cm$^{-1}$. The three samples treated with diethyl ether and water also provided equivalent FTIR spectra featuring a 2-band pattern in the region from 1200-1800 cm$^{-1}$. A comparison of FTIR spectra for the samples treated with diethyl ether ether and water showed that the samples that were dried for 12 hours are more similar than those that dried for only 10 minutes. And, the samples that dried for 12 hours provided spectra that were nearly free of broad features at >3300 cm$^{-1}$.

Therefore, independent of the lot of indium acetate used, treatment with diethyl ether and water converts the material to $In(O_2CCH_3)_2OH$; whereas, washing with anhydrous diethyl ether alone effects no change.

Example 2: Synthesis of $In(O_2CCH_3)_2OH$ on a Large Scale

In the glovebox, 35 g (0.120 mol, 1 equivalent) of commercially available indium acetate (Indium Corporation, Utica, N.Y.) was weighed and transferred into a 500 mL (2.89 mol, 24.1 equivalents) round-bottomed flask equipped with a stir bar. At 20° C., 300 mL (1.67 mol, 13.9 equivalents) of anhydrous diethyl ether was added to the flask followed by drop-wise addition of 30 mL of deionized water with stirring. The addition took approximately 15 minutes to complete. A granular white solid formed upon addition in contrast to the fine powder indium acetate starting material. After addition, the reaction mixture was stirred for 1 hour. The granular solid was scraped off the sides of the reaction flask followed by 30 additional minutes of stirring for a total of 90 minutes. The mixture was filtered through a M-porosity filtration/fritted funnel. The solid were washed with diethyl ether (3×150 mL) and dried at 20° C. under vacuum for 2 hours.

FTIR analysis of the solid indicated that there was a lot of water remaining in the product mixture. The solid was transferred into a 100 mL round-bottomed flask and placed in a 40° C. bath under vacuum with stirring. Material aerosolized in the vacuum line resulting in significant product loss. After stirring at 40° C. for 14 hours, 19 g of a white granular solid was isolated.

Example 3: Reaction of $In(O_2CCH_3)_2OH$ and Lauric Acid

A 100 mL three-necked round-bottomed flask was oven heated for 30 minutes followed by insertion of a thermocouple port, a septum, and a gas adapter. While hot, the flask was evacuated. Once the round-bottomed flask cooled to room temperature, nitrogen was allowed to flow into the flask followed by the addition of 2.5 grams (10 mmol, 1 equivalent) $In(O_2CCH_3)_2OH$ and 4.3 grams (21.5 mmol, 2.15 equivalents) of lauric acid. The flask was heated to 50° C. for 1 hour resulting in melting of some of the solids with additional solid remaining on the upper walls of the flask. The temperature was increased to 110° C. for 30 minutes followed by an increase in the temperature to 150° C. Once a temperature of 150° C. was reached, nitrogen was forced through the solution using a silicon oil bubbler. During the 30 minutes that the temperature was maintained at 150° C., some white fumes exit. After 30 minutes, the flask was dried under dynamic vacuum for 12 hours at 150° C. followed by cooling to room temperature. 21.54 grams (21.65 expected) of a white translucent wax was collected which was found to contain a single product by FTIR analysis.

Example 4: Synthesis of a Green InP Core Using $In(O_2CCH_3)_2OH$ as the $In^{3+}$ Precursor To a round-bottomed flask equipped with two vacuum adapters and a thermocouple pass-through was added 7.00 g (28.01 mmol, 1.00 equiv) of $In(O_2CCH_3)_2OH$, 1.80 g (8.20 mmol, 0.29 equivalents) of $Zn(O_2CCH_3)_2(H_2O)_2$, 5.20 g (13.45 mmol, 0.48 equivalents) of trioctylphosphine oxide and 14.51 g (72.44 mmol, 2.59 equivalents) of lauric acid at room temperature in open air. The flask was placed under vacuum followed by addition of pressure to <150 mtorr to de-gas the sample. The flask was placed under a positive pressure of nitrogen, and warmed to 80° C. with stirring at 300 rpm. The slow stirring prevented splattering of the melting solids. Once the solids melted, the temperature was raised to 125° C. in 10° C. increments and the stirring rate was increased to 900 rpm. At 125° C., the second gas adapter was opened to vent the headspace of the reaction vessel through an octadecene charged bubble. The gas flow rate was set to 20 L/min at the nitrogen supply. The headspace was purged for 90 minutes. The nitrogen purge was stopped and the flask was placed under dynamic pressure for 60 minutes with an increase in stirring to 1200 rpm. The flask was returned to positive pressure under nitrogen and the vacuum adapter was replaced with a rubber septum under nitrogen flow. An aliquot was taken for FTIR.

A calculation of the stoichiometry for lauric acid to $In^{3+}$ and $Zn^{2+}$ is presented in Table 1. As shown in Table 1, no excess lauric acid was used; however, the molar ratio is 2.59 because Zn uptakes 0.6 equivalents of lauric acid.

TABLE 1

Calculated Stoichiometries

|  | Amount (mmol) | Equivalent based on $In^{3+}$ |
|---|---|---|
| Lauric Acid | 72.43 | 2.59 |
| −2 ligands in $In^{3+}$ | −56.02 | −2 |
|  | 16.42 | 0.59 |
| −2 ligands in $Zn^{2+}$ | −16.40 | −0.59 |
| Residual lauric acid in round-bottom | 0.015 | 0.00 |

Excess (mmol) 0.015
Equiv Excess 0.001

The reaction mixture was quickly heated to 300° C.

A solution of 3.00 g (11.97 mmol, 0.43 equivalents) of tris(trimethylsilyl)phosphine and 12.0 g (32.38 mmol, 1.16 equivalents) of trioctylphosphine was prepared and rapidly injected into the reaction mixture when the temperature reached 300° C. Stirring was increased to 1500 rpm and the temperature was turned off. The reaction stirred for 80 seconds then the heat was removed from the flask. Stirring was maintained at a rate of 1500 rpm with cool air blown into the flask to cool the flask to below 150° C.

The reaction vessel was allowed to cool to 20° C. under a positive pressure of nitrogen before the thermocouple adapter was replaced with a rubber septum and the vessel was evacuated to a residual pressure of 300 mtorr. The flask was placed in the glovebox. Inside the glovebox, the reaction mixture was poured into a Teflon bottle and the flask was washed with toluene (2×12 mL). 37.5 mL of ethanol was added to Teflon bottle and the mixture was thoroughly shaken to precipitate the nanocrystals. The Teflon bottle was removed from the glovebox and centrifuged for 10 minutes at 4000 rpm. The supernatant was moved to the glovebox and was decanted away from the precipitated nanocrystals. The nanocrystals were dissolved in hexanes (2×8 mL) with vigorous stirring. The solution of the nanocrystals dissolved in hexanes was stored at ambient temperature under a nitrogen atmosphere.

Figure 12:
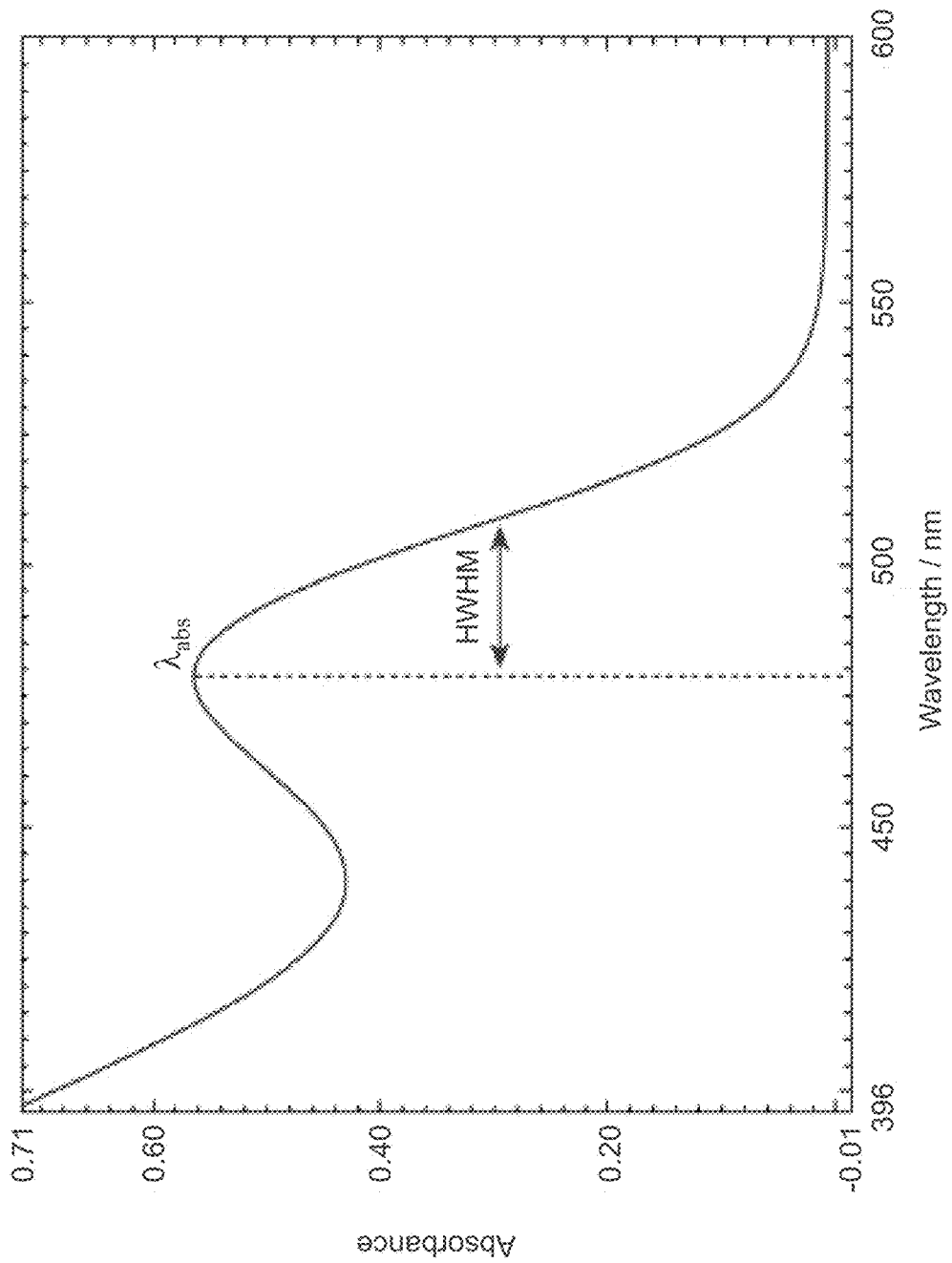
FIG. 12 is an electronic absorption spectrum of a green InP core with the maximum absorbance ($\lambda_{max}$) and half-width at half maximum (HWHM) indicated.

The product was characterized by measuring the lowest-energy electron transition (LEET). For this measurement, both the maximum absorbance ($\lambda_{abs}$) and the half-width at half maximum (HWHM) peak height were measured by electronic absorption spectroscopy for a sample of the product (0.01 mL) diluted in 8 mL of hexanes. The product was found to have a maximum absorbance of 478.6 and a half-width at half maximum of 31.2 nm as shown in FIG. 12.

Example 5: Synthesis of a Red Core Nanostructure with 0.125 Additional Equivalents of Lauric Acid Added A 100 mL round-bottomed flask was dried in an oven followed by evacuation under dynamic vacuum. Under nitrogen, 5.35 g (21.41 mmol, 1.00 equivalent) of indium acetate hydroxide, 8.93 g (23.08 mmol, 1.08 equivalents) trioctylphosphine oxide (TOPO), and 8.6 g (42.93 mmol, 2.00 equivalents) of lauric acid were added to the flask. The flask was heated to 125° C. with nitrogen at 20 L/min (with venting using a bubbler) and stirred at 1200 rpm overnight. The next day, the flask was placed under dynamic vacuum for 40 minutes. The flask was then placed under nitrogen and an additional 0.535 g (2.67 mmol, 0.13 equivalents) of lauric acid was added. The flask was heated to 320° C. at which time active heating was stopped and a solution containing both 1.5 grams (14.40 mmol, 0.67 equivalents) tris(trimethylsilyl)phosphine and 6 g (16.19 mmol, 0.76 equivalents) of trioctylphosphine was added. Stirring was increased to 1500 rpm. Samples were taken at 30, 45, 60, 75, 90, 105, 120, 180, and 240 seconds after addition.

Ultraviolet-visible spectroscopy (UV-Vis) of the product showed a broad absorption centered around 575 nm.

Example 6: Synthesis of a Green Core Nanostructure with No Additional Equivalents of Lauric Acid Added A 100 mL round-bottomed flask was dried in an oven followed by evacuation under dynamic vacuum. Under nitrogen, 3.5 g (14.00 mmol, 1.00 equivalent) of indium acetate hydroxide, 0.9 g (4.10 mmol, 0.29 equivalents) of zinc acetate hydrate, 2.6 g (6.72 mmol, 0.48 equivalents) trioctylphosphine oxide (TOPO), and 7.3 g (36.44 mmol, 2.60 equivalents) of lauric acid were added to the flask. The flask was heated to 125° C. with nitrogen at 20 L/min (with venting using a bubbler) and stirred at 1200 rpm overnight. The next day, the flask was placed under dynamic vacuum for 40 minutes. Under nitrogen, the flask was heated to 320° C. at which time active heating was stopped and 1.5 grams (5.99 mmol, 0.43 equivalents) tris(trimethylsilyl)phosphine and 6 g (16.19 mmol, 0.76 equivalents) of trioctylphosphine were added. The temperature was set at 280° C. Samples were taken at 0, 60, 75, 90, 105, 120, and 180 seconds after addition.

UV-Vis of the product showed a absorption peak centered around 470 nm that became broad if the reaction time was prolonged.

Example 7: Large Scale Synthesis of a Green Core Nanostructure with No Additional Equivalents of Lauric Acid Added A 250 mL round-bottomed flask was dried in an oven followed by evacuation under dynamic vacuum. Under nitrogen, 7.0 g (28.01 mmol, 1.00 equivalent) of indium acetate hydroxide, 1.8 g (8.203 mmol, 0.29 equivalents) of zinc acetate dihydrate, 5.2 g (13.451 mmol, 0.48 equivalents) trioctylphosphine oxide (TOPO), and 14.51 g (72.43 mmol, 2.60 equivalents) of lauric acid were added to the flask. The flask was heated to 80° C. with 300 rpm stirring to melt the solids and then the temperature was raised to 125° C. with nitrogen at 20 L/min (with venting using a bubbler) and stirred at 900 rpm overnight (approximately 14 hours). An aliquot from the reaction mixture was taken.

The next day, the flask was placed under dynamic vacuum for 90 minutes. Initially, the pressure gauge went up to 300 mtorr but it returned to between 75-100 mtorr after 10 minutes. The stirring was set to 1200 rpm for dynamic vacuum.

Under nitrogen, the flask was heated to 300° C. at which time active heating was stopped and 3.0 grams (11.97 mmol, 0.43 equivalents) tris(trimethylsilyl)phosphine and 12 g (32.38 mmol, 0.76 equivalents) of trioctylphosphine were added. The temperature was turned off and the stirring was increased to 1500 rpm.

Samples were taken at 15, 33, 45, 60, and 70 seconds after addition and after cooling.

The reaction was run for 80 seconds and then the heat was removed and the reaction mixture was allowed to air cool. UV-Vis showed an absorption maximum of 479 nm.

The reaction mixture was allowed to cool to 20° C. before the head space of the flask was evacuated and the product was placed in a glovebox. The product was dissolved in toluene and 37 mL of ethanol was added. The reaction mixture was shaken to precipitate nanocrystals and the mixture was centrifuged for 10 minutes at 4000 rpm. In the glovebox, the supernatant was discarded and the solids were isolated. The solids were suspended in n-hexanes (2×8 mL). After the washing, the product showed a maximum absorbance of 478 nm with a HWHM of 31 nm.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for preparing a compound of formula I:

$$X_1\text{—}(O_2CCH_3)_2OH \quad (I)$$

wherein $X_1$ is B, Al, Ga, In, or Tl;
the method comprising:
(1) reacting:

$$X_1\text{—}(O_2CCH_3)_{3-n}(OH)_n$$

wherein $0 < n \leq 1$; with an organic solvent and water; and
(2) drying at a temperature between about 10° C. and about 80° C.

2. The method of claim 1, wherein $0 < n < 1$.

3. The method of claim 1, wherein the organic solvent is selected from the group consisting of methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, diethyl ether, dibutyl ether, cyclopentyl methyl ether, anisole, toluene, xylene, heptanes, and mixtures thereof.

4. The method of claim 1, wherein the temperature is between about 20° C. and about 60° C.

5. The method of claim 1, wherein $X_1$ is In.

6. The method of claim 1, wherein $X_1$ is In, the organic solvent is diethyl ether, the temperature is between about 35° C. and about 45° C., and the drying is for a time between about 1 hour and about about 15 hours.

7. A method of preparing a compound of formula III:

$$X_1\text{—}(O_2C(CH_2)_bCH_3)_{3-c}(OH)_c \quad (III)$$

wherein:
$X_1$ is B, Al, Ga, In, or Tl;
b is between 7 and 19; and
c is 1 or 2;
the method comprising reacting:
(1) a compound of formula IV:

$$X_1\text{—}(OH)_a(O_2CCH_3)_{3-a} \quad (IV)$$

wherein:
$X_1$ is B, Al, Ga, In, or Tl; and
a is 1 or 2;

(2) with a compound of formula V:

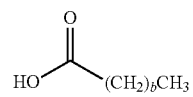

$$(V)$$

wherein:
b is between 7 and 19.

8. The method of claim 7, wherein $X_1$ is In.
9. The method of claim 7, wherein c is 2.
10. The method of claim 7, wherein b is between 7 and 12.
11. The method of claim 7, wherein the molar ratio of the compound of formula (IV) to the compound of formula (V) is between about 1:2.0 to about 1:2.8.
12. The method of claim 7, wherein $X_1$ is In, b is 10, c is 2, and wherein the molar ratio of the compound of formula (IV) to the compound of formula (V) is between about 1:2.0 to about 1:2.2.
13. A method for production of a Group III-V nanostructure, the method comprising:
(a) providing a Group III precursor prepared by the method of claim 7;
(b) providing a Group V precursor comprising a Group V atom; and
reacting the Group III and the Group V precursor to produce the nanostructure.
14. The method of claim 13, wherein the Group V precursor comprises a Group V atom substituted with an acyl group.
15. The method of claim 13, wherein the Group V precursor is a triacylphosphine.
16. The method of claim 13, wherein the Group V precursor comprises a Group V atom substituted with three unsaturated groups.
17. The method of claim 13, wherein the Group V precursor is tris(trimethylsilyl)phosphine.
18. A composition comprising:
a Group V precursor comprising a Group V atom;
a Group III precursor, wherein the Group III precursor is a compound of formula (III):

$$X_1\text{—}(O_2C(CH_2)_bCH_3)_{3-c}(OH)_c \quad (III)$$

wherein:
$X_1$ is B, Al, Ga, In, or Tl;
b is between 7 and 19; and
c is 1 or 2; and
one or more nanostructures comprising the Group III atom and the Group V atom.
19. The composition of claim 18, wherein the Group V precursor comprises a tris(trialkylsilyl) substituted Group V atom.
20. The composition of claim 18, wherein the Group V precursor is tris(trimethylsilyl)phosphine.
21. The composition of claim 18, wherein $X_1$ is In.
22. The composition of claim 18, wherein c is 2.
23. The composition of claim 18, wherein b is between 7 and 12.
24. The composition of claim 18, wherein $X_1$ is In, c is 2, and b is 10.

* * * * *